United States Patent
Tuytten et al.

(10) Patent No.: US 12,298,281 B2
(45) Date of Patent: *May 13, 2025

(54) METHOD OF PROCESSING A BIOLOGICAL SAMPLE

(71) Applicant: METABOLOMIC DIAGNOSTICS LIMITED, County Cork (IE)

(72) Inventors: Robin Tuytten, County Cork (IE); Leslie Brown, County Cork (IE); Alison E. Bond, South Wales (GB)

(73) Assignee: METABOLOMIC DIAGNOSTICS LIMITED, County Cork (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/200,053

(22) Filed: May 22, 2023

(65) Prior Publication Data

US 2023/0296570 A1  Sep. 21, 2023

Related U.S. Application Data

(63) Continuation of application No. 16/968,210, filed as application No. PCT/EP2019/053309 on Feb. 11, 2019, now Pat. No. 11,698,361.

(30) Foreign Application Priority Data

Feb. 9, 2018 (GB) ...................... 1802123

(51) Int. Cl.
G01N 30/08 (2006.01)
G01N 1/40 (2006.01)
G01N 30/34 (2006.01)
G01N 30/72 (2006.01)
G01N 30/88 (2006.01)
G01N 33/82 (2006.01)
G01N 33/92 (2006.01)

(52) U.S. Cl.
CPC ............ G01N 30/08 (2013.01); G01N 1/405 (2013.01); G01N 1/4055 (2013.01); G01N 30/34 (2013.01); G01N 30/7266 (2013.01); G01N 30/88 (2013.01); G01N 33/82 (2013.01); G01N 33/92 (2013.01); G01N 2001/4061 (2013.01); G01N 2030/8813 (2013.01); G01N 2800/368 (2013.01)

(58) Field of Classification Search
CPC ...... G01N 30/08; G01N 1/405; G01N 1/4055; G01N 30/34; G01N 30/7266; G01N 30/88; G01N 33/82; G01N 33/92; G01N 2001/4061; G01N 2030/8813; G01N 2800/368; G01N 33/689; G01N 2030/067; G01N 33/6848; G01N 30/466; G01N 30/06
See application file for complete search history.

(56) References Cited

U.S. PATENT DOCUMENTS

| | | |
|---|---|---|
| 2004/0260105 A1 | 12/2004 | Herold et al. |
| 2012/0238030 A1* | 9/2012 | Rappold .............. B01D 15/325 250/288 |
| 2014/0047906 A1 | 2/2014 | Herman et al. |
| 2014/0338432 A1 | 11/2014 | Wong et al. |
| 2015/0133336 A1 | 5/2015 | Nordlund et al. |
| 2016/0223517 A1 | 8/2016 | Kenny et al. |
| 2017/0071520 A1 | 3/2017 | Rudge et al. |
| 2018/0031585 A1 | 2/2018 | Dennis et al. |

FOREIGN PATENT DOCUMENTS

WO  2016130961 A1  8/2016

OTHER PUBLICATIONS

Kaikkonen, J., et al. "C18 hydroxy fatty acids as markers of lipid peroxidation ex vivo and in vivo." Scandinavian Journal of Clinical and Laboratory Investigation 64.5 (2004): 457-468. (Year: 2004).*
Loukotkova. "A simple and highly sensitive UPLC-ESI-MS/MS method for the simultaneous quantification of nicotine, cotinine, and the tobacco-specific carcinogens N'-nitrosonornicotine and 4-(methylnitrosamino)-1-(3-pyridyl)-1-butanone in serum samples." Journal of Chromatography B 1072 (2018): 229-234. (Year: 2017).*
Buszewski et al., "Hydrophilic interaction liquid chromatography (HILIC)—a powerful separation technique," Anal Bioanal Chem, Aug. 31, 2011, vol. 402, No. 1, pp. 231-247, DOI: 10.1007/s00216-011-5308-5. (Year: 2011).
Kenny et al., "Robust Early Pregnancy Prediction of Later Preeclampsia Using Metabolomic Biomarkers," AHA Journals, Sep. 13, 2010, vol. 56, No. 4, pp. 741-749, DOI: 10.1161/HYPERTENSIONAHA. 110.157297. (Year: 2010).

(Continued)

*Primary Examiner* — Jill A Warden
(74) *Attorney, Agent, or Firm* — Nixon Peabody LLP; David S. Resnick; Nicole D. Kling

(57) ABSTRACT

A method of processing of a biological sample containing multiple metabolites is described The method comprising the steps of pre-treating the biological sample with a metabolite extraction solvent to provide a pre-treated sample, separating a first aliquot of the pre-treated sample by reverse phase liquid chromatography (RPLC) to provide a first eluent containing resolved hydrophobic metabolites, and separating a second aliquot of the pre-treated sample by hydrophilic interaction liquid interaction chromatography (HILIC) to provide a second eluent containing resolved hydrophilic metabolites. The first and second eluents are assayed using targeted tandem mass spectroscopy operated in multiple reaction monitoring mode. Each liquid chromatography step(LC) is directly hyphenated with the tandem mass spectrometry (MS/MS) into a single LC-MS/MS analysis. The extraction solvent typically comprises methanol, isopropanol and an acetate buffer.

17 Claims, No Drawings

(56) References Cited

OTHER PUBLICATIONS

Song et al. "New instrumentation for large-scale quantitative analysis of components spanning a wide polarity range by column-switching hydrophilic interaction chromatography-turbulent flow chromatography-reversed phase liquid chromatography-tandem mass spectrometry." RSC Advances 7(51): 31838-31849 (2017).

Zhou et al. "Strategies for large-scale targeted metabolomics quantification by liquid chromatography-mass spectrometry." Analyst 141(23): 6362-6373 (2016).

\* cited by examiner

METHOD OF PROCESSING A BIOLOGICAL SAMPLE

CROSS-REFERENCE TO RELATED APPLICATIONS

This application is a continuation under 35 U.S.C. § 120 of U.S. application Ser. No. 16/968,210 filed Aug. 7, 2020 issued as U.S. Pat. No. 11,698,361 on Jul. 11,2023, which is a 35 U.S.C. § 371 National Phase Entry Application of International Application No. PCT/EP2019/053309 filed Feb. 11, 2019, which designates the U.S. and claims benefit under 35 U.S.C. § 119(a) of G.B. Application No. 1802123.8 filed Feb. 9, 2018, the contents of which are incorporated herein by reference in their entireties.

FIELD OF THE INVENTION

The present invention relates to a method of processing a biological sample, in particular a method of processing a biological sample for metabolic profiling of the biological sample. Also contemplated are methods of preparing a biological sample for liquid chromatography-mass spectroscopy metabolite analysis.

BACKGROUND TO THE INVENTION

Typically, metabolites of interest to a particular health condition are "identified" by performing so-called untargeted "discovery" studies. For example, biospecimens from two groups of individuals, one group which is exposed to the (future) health outcome ((future) "cases") and one group is not exposed to the (future) health outcome ((future) "non-cases" or "controls")), are analysed by means of a "metabolomics" analytical pipeline and then one will attempt to identify "signals" which are differential between the (future) cases and (future) controls. However, metabolite identification in untargeted mass spectrometry-based metabolomics analysis is mainly achieved through mass-based search followed by manual verification. First, the m/z value of a molecular ion of interest is searched against database(s). The metabolites having molecular weights within a specified tolerance range to the query m/z value are retrieved from the databases as putative identifications. However, putative identifications from mass-based search are rarely unique, due to the existence of isomers, and/or different chemical compositions which result in the same m/z ratio, and the limited accuracy of mass spectrometers. In some cases, one molecule ion can have more than 100 putative identifications.

Differential metabolites, which are only tentatively identified cannot be approved for clinical laboratory testing. This issue of possible compound ambiguity becomes even more pronounced, when one attempts to identify specific combinations of metabolites. So, one can only develop clinically meaningful metabolomics-based prognostic and/or diagnostic tests, when one can unambiguously extract and identify the molecules of relevance. The collection of analytical methods as elaborated in this application achieve exactly this. Other metabolomics approaches will use more targeted approaches, whereby one will use a collection of assays targeting a set of closely related metabolite compounds to look for differences between groups of individuals; typical examples include amino acid analyses, carnitine analyses or so-called "lipidomics". A major limitation of these compound-class centric approaches, is the fact that one can only achieve clinically meaningful diagnosis or prediction of complex health conditions, when combining metabolites from different compound classes, and possibly other variables. This will be exemplified extensively throughout this application.

In addition, to diagnose or predict the risk of a syndromic disease developing in asymptomatic individuals, it has become apparent that a single "biomarker" will not suffice to predict disease. What is more, achieving clinically meaningful disease risk diagnosis or prediction, either for "high risk" or for "low risk", for complex syndromes may require the development of a collection of multi-variable prognostic tests rather than a single prognostic test. To enable the discovery of multiple multi-variable prognostic tests within collections of metabolites of interest, analytical technology which can deliver precise and time- and cost-effective quantification of large collections of metabolites of interest is required.

It is an object of the invention to overcome the above-referenced problems.

SUMMARY OF THE INVENTION

The present invention addresses the need for a methodology of assaying a biological sample to unambiguously identify and quantify metabolites in the sample. The methods of the invention may be employed to detect signatures of disease, metabolic phenotypes, drug activity and efficacy, and the discovery of new biological mediators. The present invention is particularly directed to methods of metabolite profiling of biological samples to identify signatures that are diagnostic or predictive of disease, especially disorders of pregnancy (for example hypertensive disorders of pregnancy, or more specifically preeclampsia, gestational diabetes and spontaneous and non-spontaneous preterm birth). One embodiment of the methods of the invention is directed to assaying blood samples for single and multiple metabolite signatures of preeclampsia that present prior to the appearance of symptoms of the disease. The Applicants have developed a methodology that can qualitatively and quantitatively assay large numbers of metabolites (See Table 11 for an exemplary set of metabolites with relevance to hypertensive disorder of pregnancy or more specifically preeclampsia) in a high throughput, precise and robust matter, including resolution and quantitative detection of closely related metabolites such as 2-HBA and 3-HBA, leucine and isoleucine, and sphingosine-1-phosphate and sphinganine-1-phosphate, which heretofore has not been possible using MS-based techniques The methods employ pre-treatment of sample to extract metabolites (by precipitation or/and solid phase extraction), separation of metabolites in the pre-treated sample using liquid chromatography (LC), and assaying of the LC eluent by mass spectroscopy (MS). In one aspect, the Applicant has discovered that employing a dual chromatography approach, i.e. a first LC separation to provide an eluent enriched in hydrophobic metabolites, and a second LC separation to provide an eluent enriched in hydrophilic metabolites, and then assaying both eluents with MS, allows closely related metabolites to be resolved, identified and quantified accurately (Example 6). The use of targeted tandem MS in multiple reaction monitoring mode has been found to improve the specificity of profiling in the context of closely related blood-borne metabolites—in this method, a precursor ion from a compound of interest dissociates in controlled fashion and generates quantifier product ions and qualifier product ions in predictable proportions. With the identification of specific precursor ion-quantifier ion and precursor ion-qualifier ion pairs for metabolites, and more particularly for closely related blood-borne metabolites, unsurpassed specificity is achieved. In addition, or in the event no specific ion pairs can be found, monitoring the Quantifier/Qualifier ratio, has been found to provide additional assurance that the LC-MS/MS is specifically quantifying the compound of interest.

In another aspect, the Applicant has discovered that the use of tandem MS is particularly suited to profiling of metabolites related to hypertensive disorders of pregnancy, and in particular tandem MS carried out under both positive and negative electrospray ionization (Example 7). In another aspect, the Applicant has developed a metabolite extraction solvent that is capable of extracting a broad spectrum of metabolites including the metabolites that have been identified as being relevant to predicting preeclampsia (Example 2, 3 and 4). In a further aspect, the Applicant describes the use of volumetric absorptive microsampling as a means of collecting and storing liquid biological samples prior to assaying the samples for metabolites (Example 5). Although described primarily with reference to blood samples and detection of metabolites that can function as prognostic variables of preeclampsia, the methods of the invention may be applied to other biological samples such as other human and animal fluids and tissue, yeast, bacteria, cultures cells and growth media, and may be employed to detect signatures of other diseases and phenotypes, or in drug discovery/development and in basic research.

According to a first aspect of the present invention, there is provided a method of processing of a biological sample containing multiple metabolites, comprising the steps of pre-treating the biological sample by precipitation with a metabolite extraction solvent or/and by solid phase extraction to provide a pre-treated sample; treating the pre-treated sample by liquid chromatography (LC) to provide a mass spectrometry compatible eluent containing resolved metabolites, and assaying the eluent using tandem mass spectrometry.

In one embodiment, the method employs LC directly hyphenated to MS, hereafter "in-line LC-MS" or "LC-MS".

In another aspect, the invention provides a method of preparing a biological sample containing protein and multiple metabolites for mass spectroscopy metabolic profiling, comprising the steps of: mixing the biological sample with a metabolite extraction solvent, separating precipitated protein from the mixture to provide a prepared sample enriched in metabolites, in which the metabolite extraction solvent comprised methanol, isopropanol and a buffer, typically a volatile buffer, ideally an ammonium acetate buffer.

In another aspect, the invention provides a method of preparing a mass spectrometry compatible eluent containing multiple metabolites, comprising the steps of: providing an absorptive sampling device comprising a biological sample absorbed on an absorptive medium; extracting the biological sample from the absorptive sampling device into a metabolite extraction solvent to provide a mixture, separating a metabolite rich supernatant from the mixture, and performing a liquid chromatography (LC) step on the supernatant to provide a mass spectrometry compatible eluent containing multiple metabolites.

In one embodiment, the absorptive sampling device is a volume controlling sampling device, for example a VAMS device. Examples of absorptive sampling devices and volume controlling absorptive sampling devices are provided herein. In this aspect of the invention, a fixed volume of biological sample is collected and processed into a metabolite rich eluent.

In one embodiment, the metabolite extraction solvent comprises methanol, isopropanol and an ammonium acetate buffer.

In one embodiment, the metabolite extraction solvent comprises methanol, isopropanol and an ammonium acetate buffer in a ratio of about 10:9:1 (v/v/v).

In one embodiment, the biological sample is extracted from the absorptive sampling device directly into the metabolite extraction solvent.

Typically, the LC step is a dual LC step in which a first aliquot of the sample is subjected to a separation process using one form of LC to provide a first mass spectrometry compatible eluent in which metabolites of a first type are resolved from each other (e.g. hydrophobic metabolites), and a second aliquot of the sample is subjected to a separation process using a second form of LC to provide a second mass spectrometry compatible eluent in which metabolites of a second type are resolved from each other (e.g. hydrophilic metabolites). Mixtures of hydrophobic metabolites within a sample can be resolved by employing reverse phase LC (for instance, C18-, C8-, C4-, cyano-, phenyl-, pentafluorophenyl-bonded phases). Mixtures of hydrophobic metabolites within a sample can be resolved in hydrophilic metabolites by employing hydrophilic interaction LC (for instance, bare silica, diol-bonded-phase, etc).

Thus, in one embodiment, the LC step comprises separating a first aliquot of the pre-treated sample by reverse phase liquid chromatography to provide a first mass spectrometry compatible eluent containing resolved hydrophobic metabolites, separating a second aliquot of the pre-treated sample by HILIC to provide a second mass spectrometry compatible eluent containing resolved hydrophilic metabolites, and assaying the first and second eluents using on-line tandem mass spectroscopy.

In one embodiment, the RPLC employs a varying mixture of a first mobile phase (A) comprising water, methanol and a volatile buffer (e.g. an ammonium acetate buffer) and a second mobile phase (B) comprising methanol, acetonitrile, isopropanol and a volatile buffer (i.e. an ammonium acetate buffer).

In one embodiment, the RPLC mobile phases are mixed according to a varying volumetric gradient of about 1-20% (preferably about 10%) to 80-100% (preferably about 100%) mobile phase B over a suitable period, for example 1-20 minutes or about 8-12 minutes, preferably about 10 minutes. The varying volumetric gradient may be a linear gradient, or a stepwise gradient.

In one embodiment, the HILIC employs a varying mixture of a first mobile phase (A) comprising a volatile ammonium formate buffer and a second mobile phase (B) comprising acetonitrile.

In one embodiment, the HILIC mobile phases are mixed according to a varying volumetric gradient of about 80-100% (preferably about 100%) to 40-60% (preferably about 50%) mobile phase B over a period of about 8-12 minutes, preferably about 10 minutes. The varying volumetric gradient may be a linear gradient, or a stepwise gradient.

A list of mass spectrometry compatible buffers for employment in LC-MS can be found at https://www.nestgrp.com/protocols/trng/buffer.shtml In one embodiment, the biological sample comprises at least one stable isotope-labelled internal standard (SIL-IS) corresponding to a hypertensive disorder of pregnancy relevant metabolite. In one embodiment, the at least one SIL-IS is added to the biological sample prior to pre-treatment with the metabolite extraction solvent. In one embodiment, a plurality of SIL-IS's are added to the sample. In one embodiment, the at least one SIL-IS corresponds to a hypertensive disorder of pregnancy relevant metabolite. In one embodiment, the plurality of SIL-IS each independently correspond to a hypertensive disorder of pregnancy relevant metabolite. A list of relevant metabolites of hypertensive disorders of pregnancy are provided in Table 11.

In one embodiment, the plurality of hypertensive disorder of pregnancy relevant metabolites represent a plurality of metabolite classes (for example, 2, 3, 4, 5, 6, 7, 8, 9, 10, 11 or 12 classes) selected from acetyls, acyclic alkanes, acyl carnitines, aldehydes, amino acids, amino ketones, aralkylamines, benzene and substituted derivatives, tetrapyrols and derivatives, biphenyls and derivatives, carnitines, cholines, corticosteroids and derivatives, coumarins and derivatives, diacylglycerols, dicarboxylic acids, dipeptides, eicosanoids, fatty acids (including hydroperoxyl fatty acids, keto- or hydroxy-fatty acids, saturated fatty acids, unsaturated fatty acids, epoxy fatty acids), glycerophospholipids, hydroxy acids and derivatives, monosaccharide phosphates, N-acyl-alpha amino acids, phenylpropanoic acids, phosphosphingolipids, azacyclic compounds (for instance pyridines), sphingolipids, sugar alcohols, androgens and steroids (for instance testosterones), Vitamin D and derivatives.

In one embodiment, the plurality of hypertensive disorder of pregnancy relevant metabolites include at least one, a plurality, or all, of the metabolites of Table 11 (Metabolites of Interest). In one embodiment, the plurality of hypertensive disorder of pregnancy relevant metabolites include all or substantially all of 25-Hydroxyvitamin D3 (HVD3); 2-hydroxybutanoid acid (2-HBA); L-leucine (L-LEU); Citrulline (CR); Docosahexaenoic acid (DHA); Dilinoleoyl-glycerol: 1,3Dilinoleoyl-glycerol: 1,2-Dilinoleoyl-glycerol (isomer mixture) (DLG); choline (CL); L-isoleucine (L-ISO); L-methionine (L-MET); NG-Monomethyl-L-arginine (NGM); Asymmetric dimethylarginine (ADMA); Taurine (TR); Stearoylcarnitine (SC); 1-heptadecanoyl-2-hydroxy-sn-glycero-3-phosphocholine (1-HD); Biliverdin (BV); Sphingosine 1-phosphate (S-1-P); and eicosapentaenoic acid (EPO).

In one embodiment, the extraction solvent comprises methanol, isopropanol and buffer (for example a volatile buffer). In one embodiment, the buffer is an acetate buffer. In one embodiment, the acetate buffer is an ammonium acetate buffer. In one embodiment, the acetate buffer has a concentration of about 150-250 mM, preferably about 200 mM. In one embodiment, the buffer is configured to buffer the pH of the extraction solvent to about 4-5, preferably about 4.5. In one embodiment, the extraction solvent comprises methanol and isopropanol in a ratio of 5-15:5-15. In one embodiment, the extraction solvent comprises methanol and isopropanol in approximately equal amounts (i.e. 8-12: 8-12). In one embodiment, the extraction solvent comprises methanol, isopropanol and buffer in a ratio of about 10:9:1 (v/v/v).

In one embodiment, the metabolite extraction solvent comprises about 0.01% to 0.1% antioxidant (m/v). In one embodiment, the metabolite extraction solvent comprises about 0.05% antioxidant (vm/v). In one embodiment, the antioxidant is 3,5-Di-tert-4-butyl-hydroxytoluene BHT (CAS:128-37-0). Other antioxidants that could be employed include e.g., a mix of Ascorbic acid (CAS: 50-81-7) with Ethylenediaminetetraacetic acid (EDTA; CAS: 60-00-4); butylated hydroxy anisole (BHA; CAS:25013-16-5), Butylated hydroxy toluene which we use (BHT,CAS:128-37-0), and propyl gallate (PG; CAS:121-79-9).

In one embodiment, the metabolite extraction solvent is added to the biological sample in two separate aliquots and mixed after addition of the first aliquot and again after the addition of the second aliquot. In one embodiment, the solvent and sample are mixed after addition of the second aliquot. In one embodiment, the solvent and sample are mixed by vortexing.

In one embodiment, the mixture of biological sample and extraction solvent is incubated at a temperature of less than room temperature, for example less than 10° C. or 5° C. (i.e. typically less than −20° C., −10° C., −5° C., or 0° C.) for a period of time to assist protein precipitation, prior to separation of precipitated protein. In one embodiment, precipitated protein is separated by centrifugation to provide the pre-treated sample that is typically substantially free of protein and enriched in metabolites.

In one embodiment, the biological sample is a liquid sample and is collected and stored on volumetric absorptive microsampling (VAM) device. The Applicant has discovered that use of a VAM device provide for accurate control of blood sample volume, an important consideration for applications where accurate qualitative analysis of metabolites is required, such as detection or prediction of disease.

Thus, in one embodiment, the method includes the steps of providing a biological sample on an absorption medium as preferably collected with a volume-controlling sampling device which—by design—collects a controlled volume of the sample on a suitable absorption medium (for example, a volumetric absorptive microsampling device); and extracting the volumetrically obtained biological sample from such absorption medium device. In one embodiment, the biological sample is extracted from the absorption medium directly into the metabolite extraction solvent.

In one embodiment, the tandem mass spectroscopy is targeted tandem mass spectrometry. In one embodiment, the tandem mass spectrometry is carried out in multiple reaction monitoring mode.

In one embodiment, the tandem mass spectrometry comprises an ionisation technique enabling the direct analysis of an LC effluent, like electrospray ionization, and ionisation techniques derived there-of, atmospheric pressure chemical ionisation or atmospheric pressure photoionization, or continuous flow-ast atom bombardment.

When the methods of the invention are used in such way that the LC-eluent is fractionated, deposited in discrete droplets on a surface, or traced on a surface, to preserve the spatial resolution as achieved by the chromatography for later analysis, the tandem mass spectrometry can be performed using other ionization techniques also. Among them, for instance, electron ionization, chemical ionization, field desorption ionisation, matrix-assisted laser desorption ionization, surface enhanced laser desorption ionization.

In one embodiment, the tandem mass spectroscopy is carried out under both positive and negative electrospray ionization. The Applicant has discovered that in applications where multiple metabolites are being assayed, it is difficult to sufficiently charge all metabolites of interest when they all (or their fragments) need to carry the same charge. The Applicant has addressed this issue by employing a method in which the samples are assayed by tandem MS using both positive and negative electrospray ionization.

In one embodiment, the method is a method of profiling metabolites in the biological sample. In one embodiment, the method is a method of qualitative and/or quantitative profiling of metabolites in the biological sample. In one embodiment, the method is a method of qualitative and/or quantitative profiling of disorders of pregnancy related metabolites in the biological sample. In one embodiment, the method is a method of qualitative and/or quantitative profiling of preeclampsia related metabolites in the biological sample. In one embodiment, the method is a method of profiling metabolites selected from Table 11, for example all or substantially all of the metabolites of Table 11. In one embodiment, the method is a method of profiling all or substantially all of the metabolites 25-Hydroxyvitamin D3 (HVD3); 2-hydroxybutanoid acid (2-HBA); L-leucine (L-LEU); Citrulline (CR); Docosahexaenoic acid (DHA); Dilinoleoyl-glycerol: 1,3Dilinoleoyl-glycerol: 1,2-Dilinoleoyl-glycerol (isomer mixture) (DLG); choline (CL); L-isoleucine (L-ISO); L-methionine (L-MET); NG-Monomethyl-L-arginine (NGM); Asymmetric dimethylarginine (ADMA); Taurine (TR); Stearoylcarnitine (SC); 1-heptadecanoyl-2-hydroxy-sn-glycero-3-phosphocholine (1-HD); Biliverdin (BV); Sphingosine 1-phosphate (S-1-P); and eicosapentaenoic acid (EPO).

In one embodiment, the biological sample is a liquid, for example blood, or a blood derivative such as serum or plasma, as well as urine, sweat, saliva, tears, amniotic fluid, cerebrospinal fluid, or nipple aspirate. In one embodiment, the biological sample is obtained from a pregnant woman.

In another aspect, the invention provides a metabolite extraction solvent comprising methanol, isopropanol and buffer. In one embodiment, the buffer is an acetate buffer. In one embodiment, the acetate buffer is an ammonium acetate buffer. Other volatile acetate salts may be employed. In one embodiment, the acetate buffer has a concentration of about 150-250 mM, preferably about 200 mM. In one embodiment, the buffer is configured to buffer the pH of the extraction solvent to about 4-5, preferably about 4.5. In one embodiment, the extraction solvent comprises methanol and isopropanol in a volumetric ratio of about 5-15:5-15. In one embodiment, the extraction solvent comprises methanol and isopropanol in approximately equal amounts, for example a ratio of 8-12:8-12. In one embodiment, the extraction solvent comprises methanol, isopropanol and buffer in a ratio of about 10:9:1 (v/v/v). In one embodiment, the extraction solvent comprises methanol, isopropanol and ammonium acetate buffer in a ratio of about 10:9:1 (v/v/v).

In a further aspect of the present invention, there is provided a method of detecting or predicting risk of a pregnancy related disorder in a pregnant woman, the method comprising the steps of processing of a biological sample containing multiple metabolites obtained from a pregnant woman according to a method of the invention to provide a level of at least one metabolite, comparing the level of the at least one metabolite with a reference level, and detecting or predicting risk a pregnancy related disorder based on the comparison.

In another aspect of the present invention, there is provided a method of detecting or predicting risk of a pregnancy related disorder in a pregnant woman, the method comprising the steps of preparing a biological sample containing protein and multiple metabolites for mass spectrometry metabolic profiling according to a method of the invention, performing mass spectrometry metabolic profiling on the prepared sample to provide a level of at least one metabolite, comparing the level of the at least one metabolite with a reference level, and detecting or predicting risk a pregnancy related disorder based on the comparison.

In another aspect of the present invention, there is provided a method of detecting or predicting risk of a pregnancy related disorder in a pregnant woman, the method comprising the steps of preparing a mass spectrometry compatible eluent containing multiple metabolites according to a method of the invention, performing mass spectrometry metabolic profiling on the prepared sample to provide a level of at least one metabolite, comparing the level of the at least one metabolite with a reference level, and detecting or predicting risk a pregnancy related disorder based on the comparison.

Methods of comparing the level of metabolites with a reference level, and detecting or predicting risk a pregnancy related disorder based on the comparison, described in are EP3206033 and US2015168419.

Typically, mass spectrometry is LC-MS. Typically, the MS is tandem MS. Typically, the LC is dual LC. Typically, the LC-MS is in-line LC-MS. Typically, the pregnancy related disorder is selected from preeclampsia, gestational diabetes, and spontaneous and non-spontaneous pre-term birth. Typically, the sample is obtained prior to the appearance of any clinical symptoms of the early disorder of pregnancy, for example at 11-18 weeks gestation.

Other aspects and preferred embodiments of the invention are defined and described in the other claims set out below.

DETAILED DESCRIPTION OF THE INVENTION

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more", and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, elements, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies. Examples of diseases include inflammatory disease, metabolic disease, cardiovascular disease, autoimmune disease, neurological disease, degenerative disease, hepatic disease, and pulmonary disease. In one embodiment, the disease is a syndromic disorder. In one embodiment, the disease/disorder is a disorder of pregnancy, for example a hypertensive disorder of pregnancy or a metabolic disease associated with pregnancy. As used herein, the term "hypertensive disorder of pregnancy" refers to a complication of pregnancy characterised by hypertension and includes chronic hypertension (including mild and severe), gestational hypertension, preeclampsia, and eclampsia.

The term "preeclampsia" includes pre-term preeclampsia, term preeclampsia, and early onset preeclampsia. Preeclampsia is defined as elevated blood pressure after 20 weeks of gestation (140 mm Hg systolic or 90 mm Hg diastolic) plus proteinuria (>0.3 g/24 hours).

The term "pre-term preeclampsia" refers to the occurrence of preeclampsia which results to the delivery of the infant before 37 weeks of gestation.

As used herein, the term "treatment" or "treating" refers to an intervention (e.g. the administration of an agent to a subject) which cures, ameliorates or lessens the symptoms of a disease or removes (or lessens the impact of) its cause(s) (for example, the reduction in accumulation of pathological levels of lysosomal enzymes). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

As used herein, an effective amount or a therapeutically effective amount of an agent defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure.

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human.

As used herein, the term "metabolite" or "metabolites" refers to intermediates and products of metabolism, and in particular mammalian metabolism. Examples of metabolites include L-arginine, choline, adipic acid, 2-hydroxybutanoic acid, and 25-hydroxy vitamin D3. Metabolites may be classified according to metabolite class. Examples of metabolite classes include acetyls, acyclic alkanes, acyl carnitines, aldehydes, amino acids, amino ketones, aralkylamines, benzene and substituted derivatives, tetrapyrolles and derivatives, biphenyls and derivatives, carnitines, cholines, corticosteroids and derivatives, coumarins and derivatives, diacylglycerols, dicarboxylic acids, dipeptides, Eicosanoids, fatty acids (including hydroperoxyl fatty acids, keto- or hydroxy-fatty acids, saturated fatty acids, unsaturated fatty acids, epoxy fatty acids), glycerophospholipids, hydroxy acids and derivatives, monosaccharide phosphates, N-acyl-alpha amino acids, phenylpropanoic acids, phosphosphingolipids, azacyclic compounds (for instance pyridines), sphingolipids, sugar alcohols, androgens, estrogens and derivatives (for instance testosterones), Vitamin D and derivatives. In one embodiment, the invention is a method of profiling at least one metabolite from at least one of these classes. In one embodiment, the invention is a method of profiling at least one metabolite from a plurality (i.e. 2, 4, 6, 8, 10, 115 or 20) of these classes. In one embodiment, the invention is a method of profiling at least one metabolite from all or substantially all of these classes.

As used herein, the term "multiple metabolites" as applied to a biological sample refers to sample that contains at least 5 or 10 different metabolites, and in generally contains at least 20, 40, 50, 70, 90 or 100 different metabolites. The methods of the invention may be employed to profile multiple metabolites in a biological sample, and in particular provide a qualitative and quantitative profile of multiple metabolites in a biological sample.

As used herein, the term "disorder of pregnancy relevant metabolite" refers to a metabolite whose levels can be used to diagnose or predict risk of or predisposition to a disorder of pregnancy, for example, preeclampsia, gestational diabetes and spontaneous and non-spontaneous pre-term birth; examples of such metabolites are provided in Table 11. The term "substantially all of the preeclampsia relevant metabolites of Table 11" refers to at least 70%, 80% or 90% of the metabolites of Table 11.

As used herein, the term "metabolic profiling" refers to the determination of a metabolite (or preferably metabolites) in a biological sample by mass spectroscopy, preferably LC-MS, dual LC-MS, and ideally dual LC-MS/MS. The determination of metabolites in the sample may be a determination of all metabolites, or selected metabolites. Preferably, the determination is a determination of metabolites relevant to hypertensive disorders of pregnancy, especially preeclampsia. The determination of metabolites may be qualitative, quantitative, or a combination of qualitative and quantitative. In one embodiment, quantitative determination is relative quantitative determination, i.e. determination of abundance of a specific metabolite in the sample relative to a known quantity of a stable isotope labelled internal standard (i.e. SIL-IS) corresponding to the metabolite of interest. In another embodiment, quantitative determination is determined in absolute terms. Metabolic profiling of a samples can be employed in case control studies (especially nested case control studies) to identify metabolites and combinations of metabolites that can function as prognostic and diagnostic variables of disease. In one embodiment, the metabolic profiling is targeted profiling, for the determination of specific metabolites, that typically employs tuned MS settings, and generally employs electrospray ionisation—triple quadrupole (QqQ) MS/MS analysis. In one embodiment, the metabolic profiling comprises profiling of closely related metabolites. Examples include profiling of a sample containing 2-HBA and 3-HBA, or Leucine (LEU) and isoleucine (I-LEU), or sphingosine-1-phosphate and sphinganine-1-phosphate.

As used herein, the term "metabolite extraction solvent" refers to a solvent employed to extract metabolites from other components in the sample, especially protein. Generally, the solvent is an extraction/protein precipitation solvent that precipitates protein in the sample which can be separated using conventional separation technology (i.e. centrifugation or filtration), leaving a supernatant enriched in metabolites. The supernatant may then be applied to a chromatography column to resolve the metabolites in the sample and the eluent from the column may then be assayed by on-line mass spectrometry. In one embodiment, the metabolite extraction solvent comprises methanol, isopropanol and buffer. In one embodiment, the buffer is an acetate buffer. In one embodiment, the acetate buffer is an ammonium acetate buffer. Other volatile buffers or/and buffer salts may be employed, such as ammonia: acetic acid, ammonium formate, trimethylamine; acetic acid. In one embodiment, the acetate buffer has a concentration of about 150-250 mM, preferably about 200 mM. In one embodiment, the buffer is configured to buffer the pH of the extraction solvent to about 4-5, preferably about 4.5. In one embodiment, the extraction solvent comprises methanol and isopropanol in a volumetric ratio of about 5-15:5-15, or 8-12:8-12. In one embodiment, the extraction solvent comprises methanol, isopropanol and buffer in a ratio of about 10-30:10-30:1-5 (v/v/v). In one embodiment, the extraction solvent comprises methanol, isopropanol and ammonium acetate buffer in a ratio of about 10:9:1 (v/v/v).

As used herein, the term "chromatography" refers to a process in which a chemical mixture is separated into components as a result of differential distribution and or adsorption due to the differential physico-chemical properties of the components between two phases of different physical state, of which one is stationary and one is mobile.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include normal phase liquid chromatography (NPLC), reverse phase liquid chromatography (RPLC), high performance liquid chromatography (HPLC), ultra high performance liquid chromatography (UHPLC), and turbulent flow liquid chromatography (TFLC) (sometimes known as high turbulence liquid chromatography (HTLC) or high throughput liquid chromatography).

As used herein, the term "high performance liquid chromatography" or "HPLC" (sometimes known as "high pressure liquid chromatography") refers to liquid chromatography in which the degree of separation is increased by forcing the mobile phase under pressure through a stationary phase, typically a densely packed column.

As used herein, the term "ultra-high performance liquid chromatography" or "UHPLC" (sometimes known as "ultra-high pressure liquid chromatography") refers to liquid chromatography in which the degree of separation is increased by forcing the mobile phase under high pressure through a stationary phase, typically a densely packed column with a stationary phase comprising packing particles that have an average diameter of less than 2 µm.

As used herein, the term "turbulent flow liquid chromatography" or "TFLC" (sometimes known as high turbulence liquid chromatography or high throughput liquid chromatography) refers to a form of chromatography that utilizes turbulent flow of the material being assayed through the column packing as the basis for performing the separation. TFLC has been applied in the preparation of samples containing two unnamed drugs prior to analysis by mass spectrometry. See, e.g., Zimmer et al., J Chromatogr A 854: 23-35 (1999); see also, U.S. Pat. Nos. 5,968,367, 5,919,368, 5,795,469, and 5,772,874, which further explain TFLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., Turbulent Flow Analysis Measurement and Prediction, P. S. Bernard & J. M. Wallace, John Wiley & Sons, Inc., (2000); An Introduction to Turbulent Flow, Jean Mathieu & Julian Scott, Cambridge University Press (2001)).

As used herein, the term "dual liquid chromatography" or "dual LC" as applied to a biological sample refers to separation step in which a first aliquot of the sample is subjected to a first type of LC (i.e. C18 RPLC) and a second aliquot of the sample is subjected to a second type of LC (i.e. HILIC). This is especially suitable for methods of the invention in which multiple metabolites are profiled, as the dual LC separation of the sample provides for improved resolution of the metabolites, and therefore improved analytical determination. In one embodiment, the dual LC step comprises three or more chromatography steps which are performed on separate aliquots of the same sample, for example two RPLC steps which are configured to separate (different) sets of hydrophobic metabolites, and two HILIC steps which are configured to separate (different) sets of hydrophilic metabolites. This may be employed when the set of metabolites in the sample is too expansive to be adequately assayed by in-line mass spectrometry in a single dual RPLC-MS-HILIC-MS analysis.

As used herein, the term "solid phase extraction" or "SPE" refers to a process in which a chemical mixture is separated into components as a result of the affinity of components dissolved or suspended in a solution (i.e., mobile phase) for a solid through or around which the solution is passed (i.e., solid phase). In some instances, as the mobile phase passes through or around the solid phase, undesired components of the mobile phase may be retained by the solid phase resulting in a purification of the analyte in the mobile phase. In other instances, the analyte may be retained by the solid phase, allowing undesired components of the mobile phase to pass through or around the solid phase. In these instances, a second mobile phase is then used to elute the retained analyte off the solid phase for further processing or analysis. SPE, including TFLC, may operate via a unitary or mixed mode mechanism. Mixed mode mechanisms utilize ion exchange and hydrophobic retention in the same column; for example, the solid phase of a mixed-mode SPE column may exhibit strong anion exchange and hydrophobic retention; or may exhibit column exhibit strong cation exchange and hydrophobic retention.

As used herein, the term "in-line" as applied to mass spectrometry refers to mass spectrometry equipped with any ionisation source which enables the real-time ionisation of analytes present in an LC eluent which is directly and continuously led to a mass spectrometer.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., Prostate Cancer and Prostatic Diseases 1999, 2: 264-76; and Merchant and Weinberger, Electrophoresis 2000, 21: 1164-67.

As used herein, the term "tandem mass spectrometry" refers to a method involving at least two stages of mass analysis, either in conjunction with a dissociation process or a chemical reaction that causes a change in the mass or charge of an ion. The main advantage of using MS/MS is the discrimination against the chemical noise, which can originate from different sources (e.g. matrix compounds, column bleed, contamination from an ion source).

There are two different approaches in MS/MS: in space by coupling of two or more physically distinct parts of an instrument (e.g. triple quadrupole (QqQ), or Quadrupole-Time of Flight, Qq-TOF, Triple TOF, quadrupole orbitrap); or in time by performing a sequence of events in an ion storage device (e.g. ion trap, IT) or hybrids thereof (e.g., quadrupole-ion trap-orbitrap). The main tandem MS/MS scan modes are product ion, precursor ion, neutral loss, selected reaction monitoring, multiple reaction monitoring, and $MS^n$ scans.

Generally, quantitative tandem MS is performed with a triple quadrupole (QQQ) MS analyser.

MS/MS methods generally involve activation of selected ions, typically by collision with an inert gas, sufficient to induce fragmentation (collision induced dissociation, CID) and generate product ions. The product ion scan involves selection of the precursor ion of interest (using the first mass filter (Q1), its activation (q2) and a mass analysis scan (Q3) to determine its product ions. The product ion scan represents opposite process compared to the precursor ion scan; the 2nd mass filter (Q3) is set to analyse a single a product ion, whereas the first mass filter (Q1) is used to scan for precursor ions which will dissociate (in q2) into said product ion. The neutral loss scan involves scanning for a fragmentation (neutral loss of fixed, predetermined mass); Q1 and Q3 will be scanning a set m/z range in parallel, but with their filters off-set in accordance with predetermined neutral mass. It is useful for rapid screening in metabolic studies. $MS^n$ is commonly applied on ion-trap analysers. A precursor ion is selected and isolated by ejecting all other masses from the mass spectrometer. CID of the precursor ion yields ions that may have different masses (MS/MS). A product mass of an analyte is selected and other fragment ions are ejected from the cell. This product ion can be, again, subjected to CID, generating more product ions that are mass analysed (MS/MS/MS). This process can be repeated several times. However, as already mentioned, for small molecules like metabolites only MS/MS or MS/MS/MS is mainly used in practice. Selected reaction monitoring (SRM) is a special case of Selected Ion Monitoring (SIM) in which a tandem instrument is used to enhance the selectivity of SIM, by selecting both the precursor ion and the product ion. The term multiple reaction monitoring (MRM) is used if several different reactions are monitored in parallelo.

As used herein, the term "selective ion monitoring" is a detection mode for a mass spectrometric instrument in which only ions within a relatively narrow mass range, typically about one mass unit, are detected.

As used herein, "multiple reaction mode," sometimes known as "selected reaction monitoring," is a detection mode for a mass spectrometric instrument in which a precursor ion and one or more fragment ions are selectively detected. In one embodiment, the mass spectrometry of the invention employs multiple reaction mode detection that typically employs compound-specific precursor ion-quantifier ion and precursor ion-qualifier ion pairs metabolites, and optionally a step of monitoring Quantifier/Qualifier ion ratio. Under well-defined tandem mass spectrometric conditions, a precursor ion produced from a compound of interest will dissociate in controlled fashion and generate quantifier product ions and qualifier product ions in predictable proportions. By monitoring the Quantifier/Qualifier ratio, one gets additional assurance that the LC-MS/MS is specifically quantifying the compound of interest. The chance that an interference will elute at the same retention time, create the same precursor ion, and dissociate in the same quantifier and qualifier ions in the same proportion as the target of interest is deemed very low. In specific cases, the use of more than one Quantifier/Qualifier ratio can be considered. The appropriate Quantifier ion/Qualifier ion ratio (or vice versa) is established for each metabolite and SIL-IS.

As used herein, the term "operating in negative ion mode" refers to those mass spectrometry methods where negative ions are generated and detected. The term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber. As the droplets get smaller the electrical surface charge density increases until such time that the natural repulsion between like charges causes ions as well as neutral molecules to be released. Heated ESI is similar but includes a heat source for heating the sample while in the capillary tube. In one embodiment, the Agilent Jet Stream ionisation source refers to an ESI-variant using thermal gradient focusing technology to generate optimized ESI conditions.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the photoionization of molecule M is photon absorption and electron ejection to form the molecular ion $M^+$. Because the photon energy typically is just above the ionization potential, the molecular ion is less susceptible to dissociation. In many cases it may be possible to analyse samples without the need for chromatography, thus saving significant time and expense. In the presence of water vapor or protic solvents, the molecular ion can extract H to form $MH^+$. This tends to occur if M has a high proton affinity. This does not affect quantitation accuracy because the sum of $M^+$ and $MH^+$ is constant. Drug compounds in protic solvents are usually observed as $MH^+$, whereas nonpolar compounds such as naphthalene or testosterone usually form $M^+$. See, e.g., Robb et al., Anal. Chem. 2000, 72(15): 3653-3659.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase. Laser desorption thermal desorption is a technique wherein a sample containing the analyte is thermally desorbed into the gas phase by a laser pulse. The laser hits the back of a specially made 96-well plate with a metal base. The laser pulse heats the base and the heat causes the sample to transfer into the gas phase. The gas phase sample is then drawn into the mass spectrometer.

As used herein, an "amount" of an analyte in a body fluid sample refers generally to an absolute value reflecting the mass of the analyte detectable in volume of sample. However, an amount also contemplates a relative amount in comparison to another analyte amount. For example, an amount of an analyte in a sample can be an amount which is greater than a control or normal level of the analyte normally present in the sample.

As used herein, the term "biological sample" refers to biological liquids such as blood or blood derivatives (i.e. plasma, serum, buffy coat layer, platelet rich plasma, red cell preparations), saliva, cerebrospinal fluid, sweat, urine, or other biological samples including cells or tissue, bacteria, virus, fungus, cell lines, cell culture media, placenta, and amniotic fluid.

As used herein, the term "absorptive sampling device" refers to a liquid sampling device for biological material such as blood that employ an absorption medium that rapidly wicks biological fluid on to the absorption medium where the fluid is stored in a dried format. In one embodiment, the absorptive sampling device is a "volume-controlling absorptive sampling device" which is an absorptive sampling device configured to sample fluid in a volumetric, or volume controlled, fashion. Volumetric sampling is achieved by using a fixed reproducible internal volume for the absorption medium (controlling the capacity of the medium), or by controlling the volume deposited onto the absorption medium, the latter often employing microfluidic technology. One example is a "volumetric absorptive microsampling device" or "VAM device" which refers to blood sampling devices that employ a hydrophilic porous material with predefined internal volumes. They are described in EP2785859 and EP16753193 (Neoteryx LLC). Examples include the Neoteryx MITRA microsampler, available from Neoteryx of Torrence California, US. Other types of volume controlling sampling devices include DBS Systems HEMAXIS device (control of volume deposition), and HEMASPOT from SpotON Sciences (control of medium capacity). Samples collected in this way are also known as "dried liquid" or "dried blood" samples.

The analytical methods are typically based on one or more of the following:

1. the use of an extraction solvent/protein precipitation solvent that enables the extraction of the different types (classes) of metabolites. In one embodiment, the extraction solvent composition is mixture of Methanol, Isopropanol and 200 mM Ammonium Acetate (aqueous) in a 10:9:1 ratio, which in turn is fortified with 0.05% 3,5-Di-tert-4-butyl-hydroxytoluene (Example 3). The characteristics of our formulation in terms of recovery across all relevant metabolite classes, as well as in terms of reproducibility as compared to a selection of known extraction solvent compositions is exemplified. In Example 4, the ability of the formulation to extract metabolites of interest from different types of blood preparations is demonstrated. Example 5 shows that the formulation is also suitable to reproducibly extract the metabolites of interest from blood as collected by a volumetric absorptive microsampling microdevice. This is significant as the methods to analyse and quantify prognostic combinations of blood-borne metabolites, and/or metabolites together with other classes of blood-borne bio-molecules for a future health condition, depend on strict volume control of the sample. In prognosis, the biomolecules of interest are typically present in the blood of all individuals; the levels between a future-case and a future non-case will often be subtle (as all individuals at time of sampling are apparently free of the disease). For this reason, sample volume (see also Example 2) available for analysis needs to be the same for all samples at the start of the analytical process.

2. The use of a dual (High Pressure) Liquid Chromatography (LC) system to enable the identification and quantification of the different classes of metabolites in a short analytical run. The chromatographic systems were developed so that these could be directly hyphenated to a mass spectrometric detection system. This dual chromatography system was specifically developed to adequately separate the different metabolite types/classes and at the same time generate a detectable signal at the level of the mass spectrometer [Example 6]; a single chromatographic system, with short turn-around time, is not effective in robustly generating a detectable signal across all classes. The ability to 1) comprehensively analyse metabolites across different classes of metabolites, as relevant to a diagnostic or prognostic question, in 2) sufficiently short turn-around time is important to generate data on sufficiently large sample sets (necessary to enable statistically robust multivariable models) in economically viable time- and cost-frames.

3. The use of a form of quantitative mass spectrometry, i.e., a tandem mass spectrometry system (MS/MS) operated in the Multiple Reaction Monitoring (aka Single Reaction Monitoring) modus to allow for sensitive and specific analysis of metabolites (Example 7). Hereto the samples are subjected to ionization under conditions to produce ionized forms of the metabolites of interest. Then the ionized metabolites are fragmented into metabolite derived fragment ions, or product ions. Typically, the amounts of two specific fragments per metabolite are determined to identify and quantify the amounts of the originator metabolites in the sample (for further detail see below).

For each metabolite a specific LC-MS/MS assay was developed for each of the targets of interest as well as for each of the SIL-IS; a particular LC-MS/MS assay entails a combination of above points 2 & 3.

4. To unambiguously identify a metabolite/SIL-IS of interest, each of the assays will typically constitute a specific set of experimental parameters which will unequivocally identify the compound of interest. It is of note that the values of these experimental parameters are specific to and optimized for the used LC-MS/MS technology. In the case of the LC-MS/MS assays under consideration, this set of specific parameters are the following:

a. Retention time (Rt): The time between the injection and the appearance of the peak maximum (at the detector). The specific retention time is established for each metabolite.

b. Precursor ion m/z: Mass/charge ratio of the ion that is directly derived from the target compound by a charging process occurring in the ionisation source of the mass spectrometer. In this work the precursor ion is most often a protonated $[M+H]^+$ or deprotonated form $[M-H]^-$ of the target compound. In some instances, the precursor ion considered has undergone an additional loss of a neutral entity (f.i., a water molecule (H2O)) in the ionisation source. In some other instances, the ionisation of the compound of interest follows the formation of an adduct between the neutral compound and another ion (f.i, an ammonium adduct) available. The appropriate precursor ion is established for each metabolite.

c. Precursor ion charge: The charge of the ion that is directly derived from the target compound by a charging process occurring in the ionisation source of the mass spectrometer, the precursor ion can be either positively charged or negatively charged. The appropriate charge state is established for each metabolite.

d. Quantifier Product ion: Ion formed as the product of a reaction involving a particular precursor ion. The reaction can be of different types including unimolecular dissociation to form fragment ions, an ion-molecule collision, an ion-molecule reaction, or simply involve a change in the number of charges. In general, the quantifier product ion is the most intense fragment and/or specific to the compound of interest. The quantifier product ion data is used to quantify the compound of interest. The appropriate quantifier product ion is established for each metabolite and SIL-IS.

e. Qualifier Product ion: Ion formed as the product of a reaction involving a particular precursor ion. The reaction can be of different types including unimolecular dissociation to form fragment ions, an ion-molecule collision, an ion-molecule reaction, or simply involve a change in the number of charges. In general, the qualifier product ion is a less intense fragment to the compound of interest. The qualifier product ion data is used as an additional confirmation that the LC-MS/MS is specific to the compound of interest. In specific cases, the use of more than one qualifier ion is considered. The appropriate qualifier product ion is established for each metabolite and SIL-IS.

f. Quantifier ion/Qualifier ion ratio (or vice versa): under well-defined tandem mass spectrometric conditions, a precursor ion produced from a compound of interest will dissociate in controlled fashion and generate quantifier product ions and qualifier product ions in predictable proportions. By monitoring the Quantifier/Qualifier ratio, one gets additional assurance that the LC-MS/MS is specifically quantifying the compound of interest. The chance that an interference will elute at the same retention time, create the same precursor ion, and dissociate in the same quantifier and qualifier ions in the same proportion as the target of interest is deemed very low. In specific cases, the use of more than one Quantifier/Qualifier ratio can be considered. The appropriate Quantifier ion/Qualifier ion ratio (or vice versa) is established for each metabolite and SIL-IS.

Availability of the above 6 parameters will define with great certainty a highly specific assay to a compound of interest. In some instances, not all 6 parameters will be available, f.i., when the precursor ion will not dissociate in meaningful product ions.

For these metabolite targets wherefore a structurally identical SIL-IS standard is co-analysed, one has an additional specificity metric: the metabolite target and the SIL-IS have—apart from their mass—almost identical physicochemical properties, and hence they shall have the same retention time. In rare instances, perfect co-elution is not achieved due to a so-called deuterium effect, yet in these cases the difference in retention time of the metabolite and the SIL-IS will be constant and rather small.

The specific parameter sets established for exemplary metabolites and associated SIL-ISs across the metabolite classes of interest to the prediction of preeclampsia, together with some instrument specific (but non-limiting) ionization source settings are elaborated in Example 7.

5. The use of SIL-ISs to enable Stable Isotope dilution mass spectrometry, to achieve accurate and precise and accurate mass spectrometry-bases compound quantifications. In brief, Stable Isotope Dilution Mass spectrometry is based on the principle that one fortifies all study samples with the same volume of a well-defined mixture of SIL-ISs at the start of the analytical process. These SIL-IS are typically identical to the endogenous compounds of interest, in this case metabolites, but have a number of specific atoms (typically Hydrogen $^1$H, Carbon $^{12}$C, Nitrogen $^{14}$N or Oxygen $^{16}$O) within their molecular structure replaced by a stable, heavy isotope of the same element (typically Deuterium $^2$H, Carbon $^{13}$C Nitrogen $^{15}$N or Oxygen $^{18}$O). The SIL-IS are therefore chemically identical, yet have a different "heavier" mass than their endogenous counterparts. Since they are chemically identical they will "experience" all experimental variability alike the endogenous metabolites of interest. F.i., any differential extraction yield between study samples during sample preparation will equally affect the metabolite of interest and its corresponding SIL-IS. Equally, the metabolite of interest and its corresponding SIL-IS will undergo the same chromatography and are typically equally sensitive to variability during mass spectrometric analysis. As a result, the ratio of any target metabolite signal and its according SIL-IS signal are largely invariant to experimental variability, hence the ratio "metabolite signal/corresponding SIL-IS signal" is directly related to the original concentration of the target in the blood sample. So, in the here disclosed methods, the preferred way to precisely quantify the amount of a metabolite of interest in a sample is by means of establishing the ratio of "the amount of the target metabolite quantifier ion/the amount of the quantifier ion of the corresponding SIL-IS". The here disclosed methods allow one to quantify a multitude of different target metabolites in a single analysis of the sample. Moreover, as all study samples are fortified with the same volume of a well-defined mixture of SIL-IS, one can readily compare the levels of the metabolites of interest across all study samples. The SIL-IS are exogenous compounds and thus not to be found in the native biological samples, so their spiked levels act as a common reference for all study samples. The formulation of a non-limiting example of an SIL-IS mixture, as used for preeclampsia, is given in Example 1.

6. The use of specific sample processing protocols for the simultaneous processing of large batches of biospecimens with high reproducibility and low technical variability. The details of a non-limiting example of a fit-for-purpose processing protocol is given in Example 2.

EXEMPLIFICATION

The invention will now be described with reference to specific Examples. These are merely exemplary and for illustrative purposes only. They are not intended to be limiting in any way to the scope of the monopoly claimed or to the invention described. These examples constitute the best mode currently contemplated for practicing the invention.

Example 1: Preparation of Internal Standard Mixture

As relevant to the application of the methods disclosed herein, the formulation of a non-limiting example of an SIL-IS mixture, as used for preeclampsia. The SIL-IS mix was prepared by dissolving the available SIL-IS in the solvent specified in table below and making the necessary dilutions to obtain an SIL-IS mix that when spiked into plasma (10 µl of SIL-IS mix to be spiked onto 40 µl of sample) will provide the desired concentrations in plasma. Calculations for a 40 mL of SIL-IS mixture are presented; the 40 mL is made up with 50:50 MeOH:H$_2$O. Upon preparation, 1200 µL aliquots are created (serving 1 batch of 96 specimens) and stored at −20° C. until use.

TABLE 1

Composition and concentrations of SIL-IS mixture for the preeclampsia study

| SIL-IS | CAS | Individual stock solution (ng/ml) | Solvent used | SIL IS (µg in 40 ml solution) | ISTD concentration in plasma (ng/ml) |
|---|---|---|---|---|---|
| 25-Hydroxyvitamin D$_3$-[$^2$H$_3$] | CAS 140710-94-7 | 1000 | EtOH (ethanol) | 90 | 450 |
| 2-Hydroxybutyrate-[$^2$H$_3$] | CAS 1219798-97-6 | 1000 | H$_2$O | 225 | 1125 |
| 2-Methylglutaric-[$^{13}$C$_2$]*,** | CAS 1219798-68-1 | 1000 | MeOH | 200 | 800 |
| 3-Hydroxybutanoic acid [$^2$H$_4$] | CAS 1219804-68-8 | 1000 | H$_2$O | 200 | 1000 |
| 3-Methylglutaric [$_2$H$_4$]*,** | n/a | 1000 | MeOH | 500 | 2500 |
| 5-Hydroxy-L-tryptophan-[$^2$H$_3$]* | CAS 1276197-29-5 | 1000 | EtOH | 300 | 1500 |
| Hexanedioic acid [$^2$H$_8$]*,** | CAS 52089-65-3 | 2400 | MeOH | 200 | 800 |
| Adipic acid-[$^2$H$_4$] | CAS 19031-55-1 | 1000 | MeOH | 10 | 50 |
| L-Alanine-[$^{13}$C$_3$] | CAS 100108-77-8 | 10000 | H$_2$O | 2000 | 10000 |
| Arachidonic acid-[$^2$H$_8$] | CAS 69254-37-1 | 5000 | EtOH | 500 | 2500 |
| L-Arginine-[$^{13}$C$_6$] | n/a | 1000 | H$_2$O | 650 | 3250 |
| Leucine-[$^{13}$C$_6$] | n/a | 1000 | H$_2$O | 225 | 1125 |
| L-Citrulline-[$^2$H$_7$] | n/a | 1000 | H$_2$O | 250 | 1250 |
| Decanoylcarnitine-[$^2$H$_3$] | n/a | 1000 | H$_2$O | 0.5 | 2.5 |
| Dodecanoyl-L-carnitine-[$^2$H$_3$] | CAS 1021439-26-8 | 1000 | H$_2$O | 1 | 5 |
| Docosahexaenoic acid-[$^2$H$_5$] | CAS 1197205-71-2 | 1000 | MeOH | 375 | 1875 |
| 1,3-Dilinoleoyl-rac-glycerol-[$^2$H$_3$]* | n/a | 1000 | EtOH | 375 | 1875 |
| 1,3-Dilinoleoyl-rac-glycerol [$^2$H$_5$] | CAS 15818-46-9 | 1000 | EtOH | 600 | 3000 |
| Choline [$^2$H$_9$] | CAS 61037-86-3 | 2000 | H$_2$O | 1500 | 7500 |
| Homo-L-arginine [$^{13}$C$_7$, $^{15}$N$_4$] | n/a | 1000 | H$_2$O | 750 | 3750 |

TABLE 1-continued

Composition and concentrations of SIL-IS mixture for the preeclampsia study

| SIL-IS | CAS | Individual stock solution (ng/ml) | Solvent used | SIL IS (μg in 40 ml solution) | ISTD concentration in plasma (ng/ml) |
|---|---|---|---|---|---|
| Glycyl-glycine [$^{13}C_4$, $^{15}N_2$] | n/a | 1000 | MeOH | 200 | 1000 |
| Hexadecanoic acid [$^2H_4$] | CAS 75736-49-1 | 10000 | EtOH | 750 | 3750 |
| Isoleucine-[$^{13}C_6$] | n/a | 1000 | $H_2O$ | 750 | 3750 |
| Linoleic acid-[$^{13}C^{18}$] | n/a | 10000 | EtOH | 1000 | 5000 |
| L-methionine-[$^{13}C_5$] | n/a | 1000 | $H_2O$ | 300 | 1500 |
| Oleic acid-[$^{13}C_5$) | CAS 1255644-48-4 | 10000 | EtOH | 2000 | 10000 |
| 2-Oxovaleric acid [$^2H_7$]* | n/a | 100 | MeOH | 50 | 250 |
| Palmitoyl carnitine-[$^2H_3$] | n/a | 1000 | MeOH | 150 | 750 |
| Asimmetric dimethyl arginine [$^2H_6$] | CAS 1313730-20-9 | 2500 | MeOH | 12.50 | 62.50 |
| Sphingosine 1-phosphate-[$^{13}C_2$, $^2H_2$] | n/a | 1000 | MeOH | 200 | 1000 |
| Symmetric dimethylarginine-[$^2H_6$] | 1331888-08-4 | 1000 | $H_2O$ | 10 | 50 |
| Taurine [$^{13}C_2$] | CAS 70155-54-3 | 1000 | $H_2O$ | 500 | 2500 |
| L-Asparagine [$^{13}C_4$]* | n/a | 1000 | $H_2O$ | 750 | 3750 |
| Gamma-Butyrolactone [$^{13}C_2$]* | n/a | 1000 | MeOH | 32.5 | 1625 |
| N-Isobutyrylglycine-[$^{13}C_2$, $^{15}N$] | n/a | 1000 | $H_2O$ | 150 | 750 |
| Urea [$^{13}C$, $^{18}O$] | n/a | 30000 | $H_2O$ | 3600 | 18000 |
| Stearoyl-L-carnitine [$^2H_3$] | CAS 25597-09-5 | 100 | $H_2O$ | 0.2 | 1 |
| Isovaleric acid-[$^2H_9$]* | n/a | 5000 | n/a | 75 | 375 |
| Bilirubin-[$^2H_4$] | n/a | 2500 | MeOH + 0.01% $NH_3$ | 2500 | 12500 |
| Biliverdin-[$^2H_4$] | n/a | 1000 | MeOH | 225 | 1125 |
| Etiocholanolone glucuronide [$^2H_5$]* | n/a | 900 | MeOH | 45 | 225 |
| (±)-Cotinine [$^2H_3$] | CAS 110952-70-0 | 1000 | $H_2O$ | 45 | 225 |
| Myristic acid [$^2H_5$]* | n/a | 4400 | MeOH | 550 | 2750 |
| Stearic acid [$^{13}C_{18}$] | CAS 287100-83-8 | 5000 | MeOH | 1250 | 6250 |
| L-(+)-Ergothioneine [$^2H_9$] | n/a | 1000 | $H_2O$ | 1000 | 125 |
| L-Acetylcarnitine [$^2H_3$] | CAS 362049-62-5 | 1000 | $H_2O$ | 150 | 750 |
| L-Glutamine [$^{13}C_5$] | n/a | 12200 | $H_2O$ | 4880 | 24400 |

*Added to the sample, not in acquisition method;
**supplemented by means of $2^{nd}$ SIL-IS aliquot
SIL-IS were purchased from: Fluka (Arklow, Ireland), Fischer scientific (Blanchardstown, Ireland), IsoSciences (King of Prussia, PA, USA), Sigma-Aldrich (Wicklow, Ireland), Avanti Lipids (Alabaster, Alabama, USA), QMX Laboratories (Thaxted, UK), LGC (Teddington, U K), Alfa Chemistry (Holtsville, NY, USA), Generon (Maidenhead, UK), Larodan (Solna, Sweden) and R&D Systems (Abingdon, UK). Depending on physicochemical characteristics of the metabolite of interest, sometimes a salt form of the metabolite of interest was procured.

Example 2: Biospecimen Preparation Methodology

As part of the methods, a dedicated biospecimen preparation methodology has been established, involving the fortification of the samples with a relevant SIL-IS mixture (cf. Example 1), and the use of the proprietary [protein precipitation-metabolite extraction] formulation "crash", to extract the metabolites of interest. In terms of sample handling, minimizing any potential sources of error is critical to ensure reliable and precise results. The critical source of error in this methodology relates to the control of volumes; with the most critical volumes being the actual specimen volume being available for analysis, and, the volume of the SIL-IS added. Whereas experienced lab analysts will be able to prepare samples precisely, the use of robot liquid handlers, is preferred when processing large numbers of biospecimens to minimise human induced technical variability.

Here, as a non-limiting example, we elaborate a dedicated blood processing process, as relevant to methods in this application, using a liquid handling robot.

The robot was configured to enable 96 blood specimens in parallel, using the well-established 96 well format.

Instrument:

Agilent Bravo Automated Liquid Handling Platform (BRAVO, Model 16050-102, Agilent Technologies, Santa Clara, CA, USA), equipped with, a 96 LT disposable Tip Head, an orbital shaker station and a Peltier Thermal Station (Agilent Technologies). The Robot deck has 9 predefined stations, which can be used for 96 well-plates (specimens, reagents, pipette tip boxes) or functional stations (e.g. Peltier Station, etc)

Experimental Protocol:

In brief the following steps were performed for each batch of 96 40 μl aliquots; partial batches (n<96) are processed identically:

1. A 96-position plate (8×12 positions, PN:W000059X, Wilmut, Barcelona, Spain) with pre-ordered and 40 μl pre-aliquoted specimens (0.65 ml cryovials, PN:W2DST, Wilmut, Barcelona, Spain), constituting an analytical batch, are retrieved from −80° C. storage, and put on BRAVO deck (orbital shaker) and vortexed for 20 minutes to assist thawing. When thawed, the vials are decapped (manually).

2. In the meantime,
   a. a pre-prepared SIL-IS aliquot (Example 1) is retrieved from −20° C. storage for thermal conditioning, the SIL-IS is then vortexed (1 minute) and sonicated (5 minutes), and the appropriate volumes are then placed in one column (8 wells) of a PolyPropylene (PP) 96 well plate. The SIL-IS plate is then placed on the BRAVO deck (Peltier at 4° C.).
   b. the pre-prepared proprietary [protein precipitation-metabolite extraction] formulation "crash" stock was taken from −20° C. storage, stirred, and a PP 96 well plate filled with the appropriate volumes, the "crash" plate is then put on the robot deck.

3. The BRAVO protocol is then initiated, the critical steps of this process are:
   a. Draw up 140 μl of SIL-IS from the filled column of the SIL-IS plate and sequentially dispense 10 μl in each of the specimen vials.
   b. Fortified specimens will then be vortexed, on deck, for 5 min at 1200 rpm c. Addition of the "crash" solution; this part of the sample preparation is performed in two separate steps
  i. First step: addition of 200 µl "crash" solution, followed by on deck vortexing for 1 minute at 1200 rpm,
  ii. Second step: addition of 140 µl "crash" solution followed by vortexing for 4 minutes at 1000 rpm
d. The specimen plate is then removed from the BRAVO robot and vortexed at 4° C. for 10 min followed by 2 min sonication
e. Transfer of the specimen plate to the freezer, where they are kept at −20° C. for 20 minutes to maximize protein precipitation.
f. After precipitation, the specimen vials are centrifuged at 4° C. for 20 min at a speed of 8000 rpm, then they are returned to the BRAVO robot; the specimen plate is put on the Peltier station at 4° C.
g. Splitting of the supernatant (i.e., the metabolite extract) in two different aliquots to enable the separate analysis of the Hydrophobic and Hydrophilic compounds. Hereto, 240 µl of supernatant is aspirated and 120 µl is dispensed twice, into separate PP 96-well plates (duplicate "specimen extract" plates).
h. The specimen extract plates are then dried by means of vacuum evaporation at 40° C. for 60 minutes. Typically, 1 dried specimen extract plate is transferred to −80° C. until further analysis, the other specimen extract plate is returned to the BRAVO robot for re-constitution, readying the extracted specimens for LC-MS/MS analysis (cf. Examples 6&7)
  i. Hydrophobic compounds: Specimen extracts are reconstituted in 60 µl MeOH:ACN:IPA:200 mM NH4OAc at pH 4.5 (35:35:25:5), and then vortexed on deck for 5 minutes, followed by sonication (1 min).
  ii. Hydrophilic compounds: Specimen extracts are reconstituted in 60 µl H2O:MeOH:200 mM NH4OAc at pH 4.5, (92:3:5) and then vortexed on deck for 5 minutes, followed by sonication (1 min).
  iii. Note: For specimen extract plates retrieved from −80° C., a 20 min on deck thermal conditioning (room temperature) step is applied prior to reconstitution.

Whereas the above exemplified method was applied in the analysis of metabolites of interest relevant to preeclampsia; variations of the above methods are also employed as appropriate for the health outcome under consideration, and associated metabolites of interest. Non-limiting variations include 1. Pre-treatment of the sample and further extraction of metabolites using solid phase extraction instead of precipitation method; robot protocols for performing solid phase extraction are in place.
2. The consecutive addition of different SIL-IS mixtures, e.g., where there are SIL-IS which require different dissolution solvents.

Example 3: Metabolite Extraction

Underpinning the collection of methods as laid out in this application, is the capability to unambiguously identify and quantify collections of blood-borne metabolites which are, on their own and/or as part of a combination of metabolites, relevant to the diagnosis or risk prediction of a future health outcome. In this application the health condition under consideration is a pregnancy complication, more specifically but not limiting, preeclampsia. Often, targeted quantitative methods will focus on the analysis of specific compound class constituting metabolites with similar physicochemical characteristics, e.g., amino acids, or acylcarnitines or lipids etc, following the availability of an established analytical workflow for these distinct compound classes. Yet, the inventors realized that to enable the identification of non-obvious combinations of blood-borne metabolites, as required for achieving exceptional diagnosis or risk prediction, it is imperative the methods allow for the precise analysis of metabolites across functionally different metabolite classes, with different physicochemical properties, and across different concentration strata.

Moreover, as the purpose of the collection of methods elaborated herein is to deliver the specific combinations of metabolites (with or without additional variables) for (a) prognostic test(s) which can be deployed in clinical laboratories world-wide, the need for a single step metabolite extraction procedure was recognised. Furthermore, the extraction solvents used should preferably have a favourable health risk profile, in order to limit harmful exposure risks to clinically laboratory personnel.

Typically, metabolites are extracted from a biospecimen, and more specifically from a blood sample, by means of a combined [protein precipitation-metabolite extraction] step using a mainly organic solvent mixture. Depending on the physicochemical properties of the metabolite classes of interest, different solvent mixtures are commonly used. Yet, as mentioned, adequate extraction across all metabolite classes of interest, here exemplified by a collection of metabolites which are putatively of interest to predict preeclampsia risk, is mandated.

As part of the methods disclosed herein, the inventors came up with a [protein precipitation-metabolite extraction] formulation constituting Methanol (MeOH; CAS: 67-56-1), Isopropanol (IPA; CAS: 67-63-0) and an aqueous Ammonium Acetate ($NH_4OAc$; CAS: 631-61-8) buffer. In addition, the solvent was supplemented with the anti-oxidant 3,5-Di-tert-4-butyl-hydroxytoluene (BHT; CAS: 128-37-0). One of the preferred formulations entails MeOH:IPA:200 mM $NH_4OAc$ in a 10:9:1 ratio, supplemented with 0.05% (w/v) 3,5-Di-tert-4-butyl-hydroxytoluene, BHT. In the remainder of this application, this specific formulation will be identified as "crash" solvent.

In the below non-limiting example, the favourable extraction characteristics of the here disclosed formulation "crash" are illustrated by means of comparing its recovery and imprecision metrics with these of a selection of well-established, and optimized extraction solvents.

Choice of Comparators

Protein precipitation—metabolite extraction solvents were identified in the literature for the purpose of comparison with the precipitation/extraction solvent of the invention:

Want E J et al., Anal Chem, 2006, 78, 743-752, doi: 10.1021/ac051312t

Polson C et al., J Chromatogr B, 2003, 785, 263-275, doi: 10.1016/S1570-0232(02)00914-5

Dutta A et al., J Biomol Tech, 2012, 23, 128-135, doi: 10.7171/jbt.12-2304-001

Bruce S J et al., Anal Chem, 2009, 81, 3285-3296, doi: 10.1021/ac8024569

The most efficient precipitation/extraction solvents as reported in these publications were selected as comparators for the formulation of the invention,

TABLE 2

Make up of [protein precipitation-metabolite extraction] solutions considered

| Number | Solution const | mixture | Source[1] |
|---|---|---|---|
| | Proprietary solution | | |
| Ref | Formulation of the invention Methanol/Isopropanol/Ammonium acetate (200 mM aqueous), 0.05% BHT | 10:9:1 | In-house |
| | Comparators | | |
| #1 | Methanol | — | Want EJ 2005 |
| #2 | Acetonitrile | — | Polson C 2003 |
| #3 | Methanol/Ethanol | 1:1 | Bruce SJ 2009 |
| #4 | Acetonitrile/Isopropanol | 2:1 | Dutta A 2012 |
| #5 | Methanol/Acetonitrile/Acetone | 1:1:1 | Bruce SJ 2009 |
| #6 | Methanol/Chloroform/Water | 8:1:1 | Dutta A 2012 |
| #7 | Trichloroacetic acid | 10% in water (m/m) | Polson C 2003 |

Whereas in the abovementioned publications the [protein precipitation—metabolite extraction] solutions were often added in different solvent-volume to sample-volume ratios, the comparative experiment performed considered the solvent-volume to sample-volume ratio throughout, in accordance with the method as disclosed in this application (Example 2), with the exception for comparator #7.

Experimental Design

In the assessment of the [protein precipitation—metabolite extraction] solutions, 2 key metrics are considered:
1) Their ability to extract with good yield (recovery) the metabolites of interest. Here, the collection of metabolites of interest constitutes metabolites which might have relevance to the prognosis of preeclampsia.
2) Their ability to extract the metabolites of interest consistently with low imprecision (repeatability).

To assess recovery, aliquots of the same sample were extracted under identical experimental conditions with each of the 8 [protein precipitation—metabolite extraction] solutions (Example 2 Table 2.1). Next, all the extracts were fortified with the same volume of an SIL-IS mixture (cf Example 1), and the resulting samples further analysed using the analytical methods elaborated in Examples 6 and 7. For each extract, the ratio "metabolite signal/corresponding SIL-IS signal" is determined. For each metabolite of interest, the corresponding SIL-IS will undergo the same chromatography and will typically be equally sensitive to variability during mass spectrometric analysis. As a result, the ratio of any target metabolite signal and its according SIL-IS signal is directly related to the extraction yield. Because all extracts have the same amounts of SIL-IS (as added after the extraction), the extraction yields of the different [protein precipitation—metabolite extraction] solutions can be compared. To generate statistically meaningful data, identical aliquots of the same plasma sample were extracted 6 times (technical replicates) with any of the 8 [protein precipitation—metabolite extraction] solvents. Relative extraction yields for all metabolites for any of the comparators are expressed relative to the yield as obtained for the "crash" extraction. Comparator values <100% indicate an extraction yield lower than obtained with the "crash"; comparator values >100% indicate an extraction yield higher than obtained with the "crash" and comparator values of 100% indicate a yield equal to the "crash".

To assess imprecision, the same experiment as for the recovery assessment was conducted, with one key difference: all the sample aliquots were fortified with the same volume of the SIL-IS mixture (example 1) before the extraction. Since the SIL-IS are chemically identical to their metabolite counter-parts, they will "experience" all experimental variability alike the endogenous of interest and thus any differential extraction yield between the different [protein precipitation—metabolite extraction] solutions will equally affect the metabolite of interest and its corresponding SIL-IS. With the rest of the analytical work up also kept the same (cf. Examples 6&7), any differences in total analytical imprecision when comparing comparator extractions, can be attributed to the differences in extraction repeatability between comparators. Total analytical imprecision is gauged by calculating coefficients of Variation (% CV) of "metabolite signal/corresponding SIL-IS signal" for replicate extractions (n=6).

Experimental Procedure

Biospecimen used: a pool of EDTA plasma samples obtained from 10 pregnant women in $2^{nd}$ trimester of pregnancy. The plasma samples were commercially sourced from BBI solutions (Cardiff, UK). From this pool hundreds of 40 microliter aliquots were prepared in 1.5 mL polypropylene (PP) "Eppendorf" vials and stored at −80° C. until use. 96 aliquots (8 comparators*6 replicates*2 (pre-extraction spiking and post-extraction spiking of SIL-IS)) were used for the Recovery and Imprecision experiment; the two experiments were executed at the same time, by a single operator.

SIL-IS mixture used: the mixture as per Example 7 (Internal lot number: #29). [protein precipitation—metabolite extraction] solutions: all used solvents were of H PLC grade or higher, all other reagents were at least analytical grade (Methanol, Ethanol, Isopropanol, Acetonitrile, Acetone: Fisher Scientific; Chloroform, Trichloroacetic acid: Sigma Aldrich; BHT: Supelco; $NH_4OAc$: Fluka). Water was in-house ultrapure water Type 1 (@ 18MΩ).

Extraction Protocol:

The 96 EDTA 40 μL aliquots were prepared in batch, using a manual version of the method as exemplified in Example 2.

In brief the following steps were performed for each 40 μL aliquot:
1. Addition of 10 μL of SIL-IS mixture (Pre) or $H_2O$ (Post)
52. Vortex for 1 minute
3. Incubate for 15 minutes 4. Add 350 μl of [protein precipitation—metabolite extraction] solution [150 μL for #7]
5. Vortex intensively for 1 minute.
6. Store 10 minutes at 4° C.
107. Sonicate for 2 minutes
8. Place in freezer for 20 minutes
9. Centrifuge for 15 min at 14 000 rpm (15 339 g); centrifuge temperature set at 4° C.
10. Transfer 300 μL of the supernatant (extract) into second 1.5 mL PP tube [150 μl for #7]
11. Add 10 μl of water (Pre) or SIL-IS mixture (Post) to each extract
1512. Vortex 1 minute
13. Distribute each extract into 2 glass vials (1.5 mL, brown, high recovery; Agilent, Little Island, Ireland), 150 μl each [75 μl each for #7]
14. Transfer all extracts to a vacuum concentrator and evaporate extracts 90 minutes at 40° C., till dry.
2015. Store extracts at −80° C. until further analysis LC-Ms/Ms Analysis:

Prior to analysis all extracts were randomized (to avoid experimental bias), using a random number generator (Microsoft Office Excel).

The extracts were reconstituted and analysed using the methods as per Examples 6 and 7. In detail, for the hydrophobic method, samples were reconstituted in MeOH:Acetonitrile:IPA:200 mM NH$_4$OAc at pH 4.5 (35:35:25:5), whereas for the hydrophilic method samples were reconstituted in H$_2$O:MeOH:200 mM NH$_4$OAc at pH 4.5, (92:3:5).

Results

In Table 3, the extraction yields are summarized for the formulation of the invention and the various comparators. The data correspond to the responses (Metabolite signal/SIL-IS signal), with the SIL-IS spiked post-extraction. The extraction yield reported is the average over 6 technical replicates. The yields for the comparators are expressed relative to the yield of the Reference, i.e., "crash".

TABLE 3

Summary extraction yields extraction yield presented relative to extraction yield of MetaDx "crash";
Italic: recovery comparator <75% of Reference (inferior)
Bold: recovery ≥125% of Reference (superior)

| Name | Ref CRASH | #1 | #2 | #3 | #4 | #5 | #6 | #7 |
|---|---|---|---|---|---|---|---|---|
| 25-HYDROXYVITAMIN D$_3$ | 100% | *58%* | 93% | *65%* | 108% | 75% | *59%* | *31%* |
| 2-HYDROXYBUTANOIC ACID | 100% | 130% | *53%* | 121% | 105% | 104% | 145% | 98% |
| 3-HYDROXYBUTANOIC ACID | 100% | 151% | *41%* | 121% | 101% | 107% | 152% | 84% |
| L-ALANINE | 100% | 136% | *27%* | 118% | 78% | 100% | 140% | 107% |
| ARACHIDONIC ACID | 100% | 85% | 78% | 87% | 105% | 82% | 130% | *0%* |
| L-ARGININE | 100% | 116% | *7%* | 94% | *19%* | *37%* | 138% | 108% |
| L-LEUCINE | 100% | 137% | *59%* | 116% | 98% | 94% | 137% | 101% |
| 8,11,14 EICOSATRIENOIC ACID | 100% | 88% | *71%* | 91% | 106% | 84% | 128% | *2%* |
| CITRULLINE | 100% | 121% | *14%* | 114% | *49%* | 91% | 134% | 92% |
| DECANOYLCARNITINE | 100% | 138% | 108% | 99% | 101% | 96% | 135% | *8%* |
| DODECANOYL-L-CARNITINE (C12) | 100% | 119% | 105% | 108% | 107% | 99% | 135% | *0%* |
| DOCOSAHEXAENOIC ACID | 100% | 97% | 80% | 94% | 93% | 87% | 121% | *0%* |
| DILINOLEOYL-GLYCEROL+ | 100% | *65%* | *24%* | *72%* | 98% | *67%* | *68%* | *0%* |
| CHOLINE | 100% | 117% | 87% | 103% | 120% | 112% | 111% | 100% |
| HOMO-L-ARGININE | 100% | 115% | *7%* | 95% | *20%* | *37%* | 130% | 106% |
| HEXADECANOIC ACID | 100% | 87% | *43%* | 89% | 96% | 83% | 118% | *9%* |
| L-ISOLEUCINE | 100% | 129% | *55%* | 111% | 94% | 95% | 132% | 95% |
| LINOLEIC ACID | 100% | 93% | *55%* | 91% | 93% | 86% | 117% | *1%* |
| L-METHIONINE | 100% | 122% | *52%* | 105% | 89% | 93% | 132% | 85% |
| NG-MONOMETHYL-L-ARGININE | 100% | 110% | *8%* | 94% | *27%* | *43%* | 118% | 86% |
| OLEIC ACID | 100% | 89% | *46%* | 88% | 87% | 83% | 120% | *0%* |
| L-PALMITOYLCARNITINE | 100% | 92% | 83% | 100% | 92% | 86% | 115% | *0%* |
| ASYMMETRIC DIMETHYLARGININE | 100% | 125% | *17%* | 109% | *61%* | 76% | 141% | 97% |
| SPHINGOSINE-1-PHOSPHATE | 100% | 108% | *11%* | 101% | *31%* | 74% | 101% | *0%* |
| SPHINGANINE-1-PHOSPHATE (C18 BASE) | 100% | 94% | *0%* | 80% | *0%* | *56%* | 133% | *0%* |
| SYMMETRIC DIMETHYLARGININE | 100% | 130% | *15%* | 109% | *62%* | 78% | 139% | 101% |
| TAURINE | 100% | 144% | *34%* | 114% | 87% | 101% | 139% | 96% |
| UREA | 100% | 129% | 98% | 114% | 102% | 101% | 136% | 95% |
| STEAROYLCARNITINE | 100% | 76% | *71%* | 77% | 83% | 78% | 98% | *3%* |
| EICOSAPENTAENOIC ACID | 100% | 96% | *65%* | 75% | 93% | 87% | 114% | *0%* |
| MET-058 | 100% | 105% | 250% | 113% | 165% | 115% | 161% | *0%* |
| BILIRUBIN | 100% | *0%* | *46%* | *19%* | 100% | *66%* | *0%* | *0%* |
| BILIVERDIN | 100% | 104% | *61%* | 80% | *54%* | 92% | 154% | *0%* |
| ETIOCHOLANOLONE GLUCURONIDE | 100% | 82% | *21%* | 92% | 101% | 87% | 102% | *0%* |
| COTININE | no smokers In pooled sample | | | | | | | |
| MYRISTIC ACID | 100% | 97% | *57%* | 95% | 89% | 93% | 193% | *0%* |
| STEARIC ACID | 100% | 92% | *0%* | 96% | 101% | 93% | 144% | *0%* |
| L-(+)-ERGOTHIONEINE | 100% | 246% | *0%* | 247% | 152% | 170% | 321% | *1%* |

TABLE 3-continued

Summary extraction yields extraction yield presented relative to extraction yield of MetaDx "crash";
Italic: recovery comparator <75% of Reference (inferior)
Bold: recovery ≥125% of Reference (superior)

| Name | Ref CRASH | #1 | #2 | #3 | #4 | #5 | #6 | #7 |
|---|---|---|---|---|---|---|---|---|
| 20-CARBOXY-LEUKOTRIENE B4 | 100% | 89% | *48%* | 89% | 94% | 80% | 127% | *0%* |
| 1-PALMITOYL-2-HYDROXY-SN-GLYCERO-3-PHOSPHOCHOLINE (LYSOPC(16:0)) | 100% | 95% | *74%* | 96% | 94% | 88% | 128% | *0%* |
| L-ACETYLCARNITINE | 100% | 130% | *49%* | 115% | 101% | 104% | 130% | 94% |
| L-LYSINE | 100% | 116% | *9%* | 102% | *28%* | *74%* | 126% | 115% |
| MIXTURE OF [L-GLUTAMINE & 2-METHYLGLUTARIC ACID] | 100% | 127% | *17%* | 109% | 60% | 91% | 159% | 305% |

+read-out is a combined signal of 1,3-rac-Dilinoleoyl-glycerol and 1,2-rac-Dilinoleoyl-glycerol

TABLE 4

Summary precision data

Imprecision
% Coefficient of Variation (% CV)
Italic: % CV > 25%-indicative for poor extraction repeatability
Bold: % CV ≤ 15%-indicative for good extraction repeatability

| Name | Ref CRASH | #1 | #2 | #3 | #4 | #5 | #6 | #7 |
|---|---|---|---|---|---|---|---|---|
| 25-HYDROXYVITAMIN D3 | 15% | *29%* | *39%* | *33%* | *36%* | 19% | 21% | *81%* |
| 2-HYDROXYBUTANOIC ACID | 12% | 17% | 14% | 22% | 14% | 9% | 10% | *27%* |
| 3-HYDROXYBUTANOIC ACID | 7% | *27%* | 9% | *37%* | 8% | 12% | 11% | 16% |
| L-ALANINE | 8% | 17% | 19% | 19% | 18% | 9% | 6% | *105%* |
| ARACHIDONIC ACID | 10% | 23% | *56%* | 25% | 19% | 11% | 8% | |
| L-ARGININE | 7% | 21% | *29%* | 25% | 13% | 6% | 8% | 15% |
| L-LEUCINE | 6% | 21% | 19% | *29%* | 15% | 7% | 9% | 18% |
| 8,11,14 EICOSATRIENOIC ACID | 7% | 22% | *52%* | 23% | 19% | 13% | 5% | |
| CITRULLINE | 11% | 25% | 25% | *34%* | 17% | 12% | 9% | 23% |
| DECANOYLCARNITINE | 21% | 13% | *26%* | 19% | 16% | 10% | 15% | 19% |
| DODECANOYL-L-CARNITINE (C12) | 9% | 23% | *46%* | *29%* | 17% | 9% | 7% | |
| DOCOSAHEXAENOIC ACID | 7% | 21% | *56%* | *26%* | 18% | 6% | 5% | |
| DILINOLEOYL-GLYCEROL+ | 17% | 24% | *39%* | 20% | 21% | 11% | *32%* | |
| CHOLINE | 10% | 20% | *30%* | 22% | 18% | 6% | 13% | 20% |
| HOMO-L-ARGININE | 4% | 21% | *28%* | 22% | 10% | 7% | 8% | 14% |
| HEXADECANOIC ACID | 8% | 21% | *51%* | 17% | 14% | 7% | 5% | *87%* |
| L-ISOLEUCINE | 10% | 19% | 12% | 21% | 13% | 7% | 8% | 17% |
| LINOLEIC ACID | 9% | 19% | *39%* | 23% | 10% | 5% | 4% | *49%* |
| L-METHIONINE | 8% | 14% | 9% | *28%* | 20% | 8% | 9% | 19% |
| NG-MONOMETHYL-L-ARGININE | 17% | 13% | *58%* | *34%* | 25% | *49%* | 20% | 15% |
| OLEIC ACID | 9% | 20% | *44%* | 21% | 13% | 5% | 5% | |
| L-PALMITOYLCARNITINE | 5% | 25% | *61%* | 20% | 13% | 20% | 16% | |
| ASYMMETRIC DIMETHYLARGININE | 11% | 23% | *31%* | 24% | 12% | 7% | 10% | 21% |
| SPHINGOSINE-1-PHOSPHATE | 10% | *40%* | *42%* | 20% | *66%* | 11% | 14% | |
| SPHINGANINE-1-PHOSPHATE (C18 BASE) | *36%* | 17% | | *27%* | | *34%* | *31%* | |
| SYMMETRIC DIMETHYLARGININE | 10% | 17% | *29%* | *32%* | 25% | 11% | 7% | 17% |
| TAURINE | 14% | 21% | 14% | *37%* | *27%* | 13% | 11% | 21% |
| UREA | 9% | 20% | 24% | 24% | 14% | 4% | 10% | 17% |
| STEAROYLCARNITINE | 10% | 18% | *62%* | 15% | 12% | 15% | *243%* | *78%* |
| EICOSAPENTAENOIC ACID | 8% | 17% | *62%* | 13% | 18% | 21% | 17% | |
| 1-HEPTADECANOYL-2-HYDROXY-SN-GLYCERO-3-PHOSPHOCHOLINE | 13% | *30%* | 18% | 16% | *40%* | 11% | *34%* | *61%* |
| BILIRUBIN | 14% | | *145%* | 25% | 17% | *26%* | | |
| BILIVERDIN | 18% | 20% | *68%* | *32%* | *29%* | 15% | 8% | |
| ETIOCHOLANOLONE GLUCURONIDE | 13% | *26%* | *33%* | 21% | 20% | 6% | 12% | |
| COTININE | | | | no smokers In pooled sample | | | | |
| MYRISTIC ACID | 3% | *26%* | *40%* | 24% | 16% | 14% | 17% | |
| STEARIC ACID | 13% | 18% | | *27%* | 20% | 8% | *33%* | |
| L-(+)-ERGOTHIONEINE | 18% | 21% | | 21% | *38%* | 24% | 19% | *245%* |

TABLE 4-continued

Summary precision data

Imprecision
% Coefficient of Variation (% CV)
Italic: % CV > 25%-indicative for poor extraction repeatability
Bold: % CV ≤ 15%-indicative for good extraction repeatability

| Name | Ref CRASH | Comparators #1 | #2 | #3 | #4 | #5 | #6 | #7 |
|---|---|---|---|---|---|---|---|---|
| 20-CARBOXY-LEUKOTRIENE B4 | 13% | *26%* | *47%* | *30%* | *26%* | 11% | *25%* | |
| 1-PALMITOYL-2-HYDROXY-SN-GLYCERO-3-PHOSPHOCHOLINE (LYSOPC(16:0)) | 8% | 17% | *27%* | 23% | 10% | 4% | 13% | *58%* |
| L-ACETYLCARNITINE | 8% | 18% | 12% | 24% | 13% | 6% | 8% | 17% |
| L-LYSINE | 10% | 20% | *39%* | 15% | 13% | 13% | 10% | 22% |
| MIXTURE OF [L-GLUTAMINE & 2-METHYLGLUTARIC ACID] | 10% | 18% | 24% | *25%* | 13% | 11% | 12% | *43%* |

+read-out is a combined signal of 1,3-rac-Dilinoleoyl-glycerol and 1,2-rac-Dilinoleoyl-glycerol In Table 4, the imprecision data are summarized for the formulation of the invention and the various comparators. The data correspond to the responses (Metabolite signal/SIL-IS signal), with the SIL-IS spiked pre-extraction. The percent coefficient of variation (% CV) is calculated for 6 technical replicates.

In terms of recovery, comparators #2 and #7 are clearly inferior. Comparators #4 and #5 result, in general terms, in lower extraction yields compared to the proprietary crash, whereas #4 also fails to extract one of the metabolites of interest. Comparators #1 delivers largely similar extraction yields, and #6 results in favourable recovery for many of the targets of interest, yet both comparator #1 and #6 do fail to extract some metabolites altogether. Additionally, it should be noted that comparator #6, albeit a very efficient extraction solvent for the majority of metabolites, it contains chloroform which is a CMR substance and should be avoided in laboratory procedures when possible. Comparator #3 delivers yields similar to the proprietary "crash". Only comparators #3 and #5 and the proprietary "crash" do extract all the metabolites of interest.

In terms of imprecision, the proprietary "crash" clearly stands out, with an imprecision ≥25% CV for only one metabolite of interest. In view of using metabolite measurements and/or combinations of metabolite measurements in diagnosis or risk prediction of a future health outcome, good reproducibility is even more important than superior extraction yields. Taking the recovery and imprecision data together, the exemplary data as shown here confirm that the novel formulation, "crash", as developed by the inventors, is superior to all other tested [protein precipitation—metabolite extraction] solvents, making this "crash" solvent, and, or derived compositions thereof, highly suited for the aims as laid out in this application.

Example 4: Extraction of Metabolites from Different Types of Blood

In the below non-limiting example, the abilities of the protein precipitation-metabolite extraction formulation of the invention (cf. Example 3) to extract metabolites of interest from different type of blood work-ups. Extraction figure of merits are compared for EDTA plasma and serum, being typical blood derivatives, whereby the former served as the reference. For the sole reason of exemplifying, the following metrics were considered; i.e., recovery, precision and linearity (calibration).

Experimental Design

Recovery: To compare the performance of the "crash", the recovery of any of the SIL-ISs, as part of the SIL-IS mixture (cf. example 1), is assessed for EDTA plasma and serum, whereby both were obtained from pregnant women in their $2^{nd}$ trimester of pregnancy (BBI Solutions, Cardiff, UK). The use of the SIL-IS metabolites to compare EDTA plasma vs serum extractions is adopted as it is independent of any differential metabolite levels between EDTA plasma and serum; moreover, the EDTA plasma and serum samples were collected from different individuals.

Sample processing and analysis were executed as elaborated in Example 6, 7 and 2. For both EDTA plasma and serum, extraction yields are estimated by comparing the average SIL-IS metabolite signal in 6 replicate samples wherefore the SIL-IS is spiked in the sample before extraction (pre-extraction) with the average SIL-IS metabolite signal in 6 replicate samples wherefore the SIL-IS is spiked in the sample after extraction (post extraction). The ratio (average SIL-IS metabolite signal pre-extraction)/(average SIL-IS metabolite signal post-extraction) are calculated for each available SIL-IS in either plasma and serum. Then the metabolite extraction yields as achieved in EDTA plasma with the "crash" were set as the reference (100%). The corresponding relative yields in serum were then also calculated.

Imprecision: In view of the collection of methods disclosed in this application, the ability to extract the metabolites of interest with high reproducibility (precision) is important (cf. also Example 3). To assess imprecision, the metabolites of interest as present in the EDTA plasma samples and Serum samples were analysed (6 replicates of each), as per Example 5&6, in the same experiment. As the analytical work up is identical for both the EDTA plasma and serum samples, any differences in total analytical imprecision can be attributed to the differences in sample matrix, i.e., EDTA plasma vs. serum. Total analytical imprecision is gauged by calculating coefficients of Variance (% CV) of "metabolite signal/corresponding SIL-IS signal" for replicate extractions (n=6). Imprecision data were compiled and assessed.

Calibration: In view of the collection of methods disclosed in this application, the ability to (relatively) quantify the metabolites of interest is important; i.e., one should be able to differentiate a high level of metabolite from a low level of metabolites as present in different (patient) samples. Quantification is often done by establishing calibration curves across a (relevant) range and reading the level of an unknown sample from such curve. As part of the Quality Assurance methods, calibration curves for all the metabolites of interest are established. To assess whether the proprietary [protein precipitation—metabolite extraction] solution formulation ("crash") supports quantification in serum also, a single 8-point calibration curve was prepared in serum (Technopath, Tipperary, Ireland) in an identical way to that used for EDTA plasma. Calibration curves were plotted, and an appropriate calibration function was established using (linear) regression. Assessment of $r^2$ (correlation coefficient—squared) is used to assess goodness of fit and as used as an indicator of whether metabolite extraction with the "crash" formulation supports quantification across the metabolites of interest.

Results

In Table 5, the results for the recovery, precision and calibration assessments are summarized for the extractions of EDTA plasma and serum using the proprietary "crash" formulation. Data in bold are considered of high quality (respectively superior relative extraction yield >125% of the reference, low imprecision % CV≤15%, or $r^2$>0.98), whereas the italic values are considered of low quality (respectively inferior relative extraction yield <75% of the reference, high imprecision % CV>25%, or $r^2$<0.90).

Not all corresponding SIL-IS were available, hence the empty values in ISTD Recovery. The empty value in the "precision" metric would correspond to below "limit of detection" levels for these metabolites of interest within the analytical framework used.

TABLE 5

Comparison of extraction metrics for serum vs. EDTA plasma

| Metabolite | ISTD Recovery Plasma | ISTD Recovery Serum Relative | Precision Plasma | Precision Serum | $r^2$ Plasma | $r^2$ Serum |
|---|---|---|---|---|---|---|
| 25-HYDROXYVITAMIN D$_3$ | 100% | 99% | *33.0%* | 15.0% | 0.992 | 0.901 |
| 2-HYDROXYBUTANOIC ACID | 100% | 99% | 3.3% | 1.3% | 0.990 | 0.987 |
| 3-HYDROXYBUTANOIC ACID | 100% | 88% | 7.6% | 4.2% | 0.992 | 0.990 |
| ADIPIC ACID | 100% | 78% | *53.1%* | *39.8%* | 0.977 | *0.746* |
| L-ALANINE | 100% | 110% | 5.5% | 4.5% | 0.991 | 0.992 |
| ARACHIDONIC ACID | 100% | 118% | 13.0% | 7.2% | 0.982 | 0.995 |
| L-ARGININE | 100% | 118% | 3.5% | 2.6% | 0.994 | 0.995 |
| L-LEUCINE | 100% | 105% | *27.0%* | *37.4%* | 0.996 | 0.991 |
| 8,11,14 EICOSATRIENOIC ACID | | | 9.6% | 4.4% | 0.991 | 0.999 |
| CITRULLINE | 100% | 113% | 10.5% | 5.0% | 0.994 | 0.982 |
| DECANOYLCARNITINE | 100% | 138% | 13.0% | 9.0% | 0.985 | 0.980 |
| DODECANOYL-L-CARNITINE (C12) | 100% | 134% | 9.1% | 3.0% | 0.993 | 0.995 |
| DOCOSAHEXAENOIC ACID | 100% | 124% | 3.7% | 4.6% | 0.992 | 0.998 |
| DILINOLEOYL-GLYCEROL⁺ | 100% | 130% | 8.0% | 7.1% | 0.987 | 0.982 |
| CHOLINE | 100% | 100% | 1.7% | 18.4% | 0.994 | 0.993 |
| GLYCYL-GLYCINE | 100% | 118% | 3.9% | 7.0% | 0.985 | *0.831* |
| HOMO-L-ARGININE | 100% | 114% | 5.1% | 4.4% | 0.992 | 0.997 |
| HEXADECANOIC ACID | 100% | 118% | 7.3% | 3.6% | 0.990 | 0.987 |
| L-ISOLEUCINE | 100% | 91% | 6.7% | 3.2% | 0.990 | 0.997 |
| LINOLEIC ACID | 100% | 123% | 6.2% | 3.7% | 0.993 | 0.998 |
| L-METHIONINE | 100% | 146% | 3.0% | 2.6% | 0.997 | 0.995 |
| NG-MONOMETHYL-L-ARGININE | | | 5.7% | 15.3% | 0.963 | 0.957 |
| OLEIC ACID | 100% | 118% | 3.8% | 4.0% | 0.991 | 0.995 |
| L-PALMITOYLCARNITINE | 100% | 134% | 5.0% | 5.6% | 0.990 | 0.997 |
| ASYMMETRIC DIMETHYLARGININE | 100% | 109% | 2.9% | 4.8% | 0.995 | 0.989 |
| SPHINGOSINE-1-PHOSPHATE | 100% | 175% | 11.2% | 3.5% | 0.910 | 0.985 |
| SPHINGANINE-1-PHOSPHATE (C18 BASE) | | | 16.5% | 10.9% | 0.930 | 0.932 |
| SYMMETRIC DIMETHYLARGININE | 100% | 102% | 5.5% | 6.9% | 0.992 | 0.998 |
| TAURINE | 100% | 104% | 7.3% | 6.6% | 0.992 | 0.994 |
| ISOBUTYRYLGLYCINE | 100% | 118% | *39.8%* | *37.5%* | 0.986 | 0.963 |
| UREA | 100% | 115% | 3.4% | 3.9% | 0.995 | 0.997 |
| STEAROYLCARNITINE | 100% | 135% | 2.0% | 6.5% | 0.992 | 0.977 |
| RICINOLEIC ACID | | | 6.5% | 5.5% | 0.991 | 0.969 |
| 13-OXOOCTADECANOIC ACID | | | | | 0.988 | 0.998 |
| 3-HYDROXYTETRADECANOIC ACID | | | | | 0.964 | 0.967 |
| 1-HEPTADECANOYL-2-HYDROXY-SN-GLYCERO-3-PHOSPHOCHOLINE | | | 17.5% | *38.2%* | 0.988 | *0.754* |
| BILIRUBIN | | | *31.7%* | 3.7% | 0.960 | 0.968 |
| BILIVERDIN | 100% | 70% | 14.0% | 10.4% | 0.996 | 0.983 |
| ETIOCHOLANOLONE GLUCURONIDE | | | 3.5% | 6.8% | 0.992 | 0.973 |
| COTININE | 100% | 97% | *28.0%* | *34.9%* | 0.992 | 0.980 |
| MYRISTIC ACID | | | 14.0% | 5.4% | 0.989 | 0.990 |
| STEARIC ACID | | | *41.3%* | 23.0% | 0.961 | 0.957 |

TABLE 5-continued

Comparison of extraction metrics for serum vs. EDTA plasma

| Metabolite | ISTD Recovery Plasma | Serum Relative | Precision Plasma | Serum | $r^2$ Plasma | Serum |
|---|---|---|---|---|---|---|
| L-(+)-ERGOTHIONEINE | 100% | 133% | *27.8%* | 14.6% | 0.995 | 0.965 |
| 20-CARBOXY-LEUKOTRIENE B4 | | | 19.7% | 13.0% | 0.973 | 0.981 |
| 2-HYDROXYTETRADECANOIC ACID | | | | | 0.968 | 0.963 |
| 1-PALMITOYL-2-HYDROXY-SN-GLYCERO-3-PHOSPHOCHOLINE (LYSOPC(16:0)) | | | 5.2% | 6.7% | 0.993 | 0.994 |
| L-ACETYLCARNITINE | 100% | 100% | 3.1% | 1.7% | 0.990 | 0.994 |
| L-LYSINE | | | *29.7%* | 6.7% | 0.958 | 0.938 |
| MIXTURE OF [L-GLUTAMINE & 2-METHYLGLUTARIC ACID] | 100% | 310% | 5.0% | 5.6% | 0.994 | 0.990 |

⁺read-out is a combined signal of 1,3-rac-Dilinoleoyl-glycerol and 1,2-rac-Dilinoleoyl-glycerol From Table 5, it can be concluded that the precipitation/extraction formulation of the invention enables for the effective and quantifiable extraction of metabolites of interest across all relevant metabolite classes from both Serum and EDTA Plasma.

Taken the exemplary but non-limiting recovery, imprecision and calibration data together, the data as shown here confirm that the novel formulation, "crash", as developed by the inventors, is suitable to extract metabolites of interest across metabolite classes with different physicochemical properties from different types of blood specimens. This confirms this "crash" solvent, and, or derived compositions thereof, highly suited for the aims as laid out in this application.

Example 5: Extraction Using Volumetric Absorptive Microsampling Device

A non-limiting example of the ability of the precipitation/extraction formulation of the invention to extract metabolites of interest from blood samples collected with a volumetric absorptive microsampling device is also exemplified (Neoteryx 20 µl Mitra Microsamplers, Neoteryx, CA, USA). This type of volumetric absorptive microsampling device, is similar to dried blood spot (DBS) technology. Hence, the term "DBS" will be used throughout when discussing the collection of all such sample collection technologies.

In view of the aims of the collection of methods disclosed herein, i.e, the development of novel prognostic tests which can be easily deployed in different clinical health care settings worldwide, and more specifically in first-line prenatal care settings, the use of DBS technology is an attractive alternative to conventional venous plasma sampling.

Ease of use: DBS is less invasive than conventional whole blood, plasma, or serum sample collection because the blood can be collected after a small finger prick (or heel prick for paediatric applications). Because of the ease of collection, DBS can be obtained in a non-hospital environment by minimally trained technicians or even at home by the patients themselves. Moreover, the DBS process does not necessarily require use of an anticoagulant, or plasma separation, which limits the number of manipulations. The possibility to collect blood samples without the need for a trained phlebotomist will significantly facilitate the roll-out of prognostic tests, as considered in this application, in low and medium resource settings.

Cost-effective process: the cost of shipping/storage of DBS samples is substantially reduced, because DBS samples can typically be stored at room temperature, alleviating the need for cold logistic chain transport of blood specimens to a central clinical laboratory; this will again significantly enable the roll-out of diagnostic or prognostic tests, as considered in this application, in low and medium resource settings.

Analyte stability: it has been reported in numerous publications that specimens collected using DBS and stored over many months (even years) at ambient temperature are just as stable as plasma samples that were stored at −20° C.

Improved safety: during drying, most of the pathogenic agents are deactivated on DBS media, which reduces the risk of infection to a minimum. Similarly, transfer of blood material on to a DBS medium is considered to have a low infection risk.

In view of the methods considered here, typical DBS collections, i.e., spotting a drop of blood on specific types of filter paper cards, cannot be used, as they do not control the blood sample volume being collected. The prognostic tests being disclosed herein are based on the analysis of metabolites of interest (possibly in combination with other compounds circulating in an individual's blood), which are always present irrespective of the (future) health outcome. The prognostic performance of the tests disclosed in this application is derived from the non-trivial combined changes in levels of a specific set of metabolites of interest (possibly in combination with other variables) as available in a specific volume, and the association thereof with the probability of the (future) health outcome occurring. This is very distinct from (diagnostic) applications whereby the compound of interest, as present in the biospecimen collected by DBS, is present or not present (binary), or depends on the ratio of 2 compounds. In these instances, the volume of the sample collected is irrelevant.

For this reason, the inventors realized that, in order to deploy the prognostic tests based on the use of DBS technology for blood sample collection, volume of the blood sample needs to be known and precise. This can be achieved manually by using e.g., graduated capillaries to collect the blood and then deposit the blood onto a DBS card. Differently more advanced technologies, like but not limited to, the here used Neoteryx' volumetric absorptive microsampling devices (Neoteryx, CA, US) or the HemaXis and other DBS sampling technologies of DBS system (DBS system, Gland Switzerland), or HemaSpot from Spot On Sciences (Austin, TX, US).

Here, the abilities of the precipitation/extraction formulation of the invention to extract metabolites of interest from blood specimens as collected using Neoteryx 20 µl Mitra Microsamplers, Neoteryx, CA, USA) is assessed.

Extraction figures of merits are compared for extraction of metabolites from EDTA plasma derived calibrators ($r^2$) and quality controls (precision) of which i) 40 µl were extracted in the conventional way (cf Example 2) to be used as a reference and ii) 20 µl were sampled on 20 µl Mitra Microsampler. After drying, the Mitra Microsampler devices were extracted with a protocol which was largely kept the same (cf. Examples 3 & 2) as for liquid, conventional samples, to achieve meaningful comparative data, as well as to illustrate the generic applicability of the sample processing methods as disclosed elsewhere in this application. Further analysis of the extracts by LC-MS/MS was identical and as per the methods in Examples 6 and 7.

Additionally, confirmation whether the "crash" will also extract the metabolites of interest from whole blood was investigated by sampling i) fresh EDTA whole blood and ii) fresh EDTA plasma—collected from the very same person at the very same time—with 20 µl Mitra Microsamplers. These were both extracted and analysed with the same protocol as the calibrators and QCs described above.

Experimental Execution

A set of ready-prepared calibrators and six ready prepared QC-average samples, i.e., aliquots with relative value of "40" (cf, calibration), were retrieved from the −80° C. freezer. 20 µl Neoteryx microsamplers were used to dip into the plasma for 6 seconds and then placed to dry in a desiccated bag overnight, protected from light. In addition, a freshly collected whole blood sample from a healthy female volunteer (non-pregnant) was divided into two parts and EDTA plasma was achieved by centrifugation from one part, to prepare comparable naïve plasma. Next both the naïve whole blood and the naïve plasma were collected unto a 20 µl Neoteryx microsampler and placed to dry in a desiccated bag overnight, protected from light.

The next day the Neoteryx 20 µl samplers were detached from their support in 1.2 ml polypropylene Eppendorf tubes. Next the tubes were gently shaken for 30 minutes after addition of 350 µl of the proprietary "crash" solution, whereby the "crash" solution was pre-fortified with 10 µl SIL-IS (cf. Example 1), then the tubes were sonicated for 5 minutes and transferred to a −20° C. freezer for 20 minutes; then they were shaken briefly for 3 seconds and then centrifuged for 15 minutes at 1400 rpm at 4° C. The supernatant was taken off and distributed over 2 vials (150 µl in each) and then evaporated for 1 hour at 40° C. after which one set was immediately reconstituted and analysed with HILIC-MS/MS (examples 6 & 7); the other split was stored at −80° C. till analysis with RPLC-MSMS hydrophobic analysis (examples 6 & 7).

In parallel, a $2^{nd}$ set of ready-prepared calibrators and another set of six QC-average samples (from the same batch as the ones used for sampling unto Neoteryx samplers) were extracted with the proprietary "crash" formulation and further analysed as per the generic methods (Examples 6, 7 & 2).

Extractability from Freshly Collected Specimens:

For the metabolites of interest, it was determined whether the proprietary "crash" formulation enabled their extraction and subsequent LC-MS/MS analysis from unspiked, naïve whole blood and EDTA plasma as collected/stored on a 20 µl Mitra microsampler. The assessment involved confirmation of the generation of a quantifiable read-out (Metabolite signal/SIL-IS signal ratio). The data are presented in Table 6

Imprecision: In view of the collection of methods disclosed in this application, the ability to extract the metabolites of interest with high reproducibility (precision) is important (cf. also Example 2). To assess imprecision, the metabolites of interest as present in the QC-average samples were analysed (6 replicates of each) for conventionally extracted EDTA plasma (reference), as well as from QC-average samples as resampled with microsamplers. The according precision data is also presented in Table 6

Calibration: In view of the collection of methods disclosed in this application, the ability to (relatively) quantify the metabolites of interest is important. To assess whether the proprietary "crash" supports quantification from metabolites of interest from blood samples as collected with an exemplary DBS-technology, a single 8-point calibration curve, was resampled with Neoteryx microsamplers; extracted and analysed. The calibration curve read-outs were compared with an identical curve as prepared in solution, in the same experiment. Calibration curves were plotted, and an appropriate calibration function was established using (linear) regression. Assessment of $r^2$ (correlation coefficient—squared) is used to assess goodness of fit and as used as an indicator whether metabolite extraction with the "crash" formulation supports quantification across the metabolites of interest. The according "calibration" data is also presented in Table 6.

Results

TABLE 6

Extraction metrics for blood samples on Neoteryx microsamplers as well as comparator data for naïve EDTA plasma

| | In Neoteryx Extract? | | Precision | | $r^2$ | |
|---|---|---|---|---|---|---|
| | | | conven- | EDTA | conven- | EDTA |
| | | | tionally | plasma | tionally | plasma |
| Name | Naïve whole blood | Naïve EDTA plasma | extracted EDTA plasma | extracted from Neoteryx | extracted EDTA plasma | extracted from Neoteryx |
| 25-HYDROXYVITAMIN D$_3$ | no* | no* | 16.80% | # | 0.956 | # |
| 2-HYDROXYBUTANOIC ACID | yes | yes | 6.50% | 9.40% | 0.997 | 0.998 |
| 3-HYDROXYBUTANOIC ACID | chrom | chrom | 7.40% | # | 0.989 | # |
| ADIPIC ACID | yes | yes | 20.50% | 21.60% | 0.972 | *0.896* |
| L-ALANINE | yes | yes | 12.10% | 10.30% | 0.997 | 0.965 |

TABLE 6-continued

Extraction metrics for blood samples on Neoteryx microsamplers as well as comparator data for naïve EDTA plasma

| Name | In Neoteryx Extract? Naïve whole blood | In Neoteryx Extract? Naïve EDTA plasma | Precision conventionally extracted EDTA plasma | Precision EDTA plasma extracted from Neoteryx | $r^2$ conventionally extracted EDTA plasma | $r^2$ EDTA plasma extracted from Neoteryx |
|---|---|---|---|---|---|---|
| ARACHIDONIC ACID | yes | yes | 11.10% | 6.90% | 0.993 | 0.982 |
| L-ARGININE | yes | yes | 5.90% | 5.00% | 0.999 | 0.997 |
| L-LEUCINE | yes | yes | 6.80% | 8.50% | 0.974 | 0.998 |
| 8,11,14 EICOSATRIENOIC ACID | yes | yes | 12.40% | 8.00% | 0.993 | 0.984 |
| CITRULLINE | yes | yes | 5.36% | 7.30% | 0.971 | 0.975 |
| DECANOYLCARNITINE | yes | yes | 18.00% | 18.20% | 0.978 | 0.985 |
| DODECANOYL-L-CARNITINE (C12) | yes | yes | 11.30% | 8.10% | 0.996 | 0.999 |
| DOCOSAHEXAENOIC ACID | yes | yes | 6.20% | 6.80% | 0.992 | 0.995 |
| DILINOLEOYL-GLYCEROL⁺ | yes | yes | *26.90%* | 11.20% | 0.985 | # |
| CHOLINE | yes | yes | 3.80% | 6.50% | 0.998 | 0.993 |
| GLYCYL-GLYCINE | yes | yes | 10.90% | 15.60% | 0.99 | 0.992 |
| HOMO-L-ARGININE | yes | yes | 6.40% | 8.10% | 0.999 | 0.994 |
| HEXADECANOIC ACID | yes | yes | 7.60% | 8.90% | 0.989 | 0.971 |
| L-ISOLEUCINE | yes | yes | 5.70% | 6.90% | 0.999 | 0.995 |
| LINOLEIC ACID | yes | yes | 5.60% | 6.10% | 0.998 | 0.99 |
| L-M ETHIONINE | yes | yes | 4.20% | 6.30% | 0.997 | 0.994 |
| NG-MONOMETHYL-L-ARGININE | no | no | 8.20% | 10.30% | 0.999 | 0.997 |
| OLEIC ACID | yes | yes | 5.80% | 6.10% | 0.995 | 0.997 |
| L-PALMITOYLCARNITINE | yes | yes | 10.90% | 12.60% | 0.986 | 0.993 |
| ASYMMETRIC DIMETHYLARGININE | yes | yes | 7.00% | 6.70% | 0.993 | 0.995 |
| SPHINGOSINE-1-PHOSPHATE | yes | yes | 6.40% | 10.70% | 0.998 | 0.993 |
| SPHINGANINE-1-PHOSPHATE (C18 BASE) | yes | yes | 19.40% | 13.90% | 0.987 | 0.929 |
| SYMMETRIC DIMETHYLARGININE | yes | yes | 10.20% | 11.90% | 0.991 | 0.999 |
| TAURINE | yes | yes | 5.30% | 6.30% | 0.994 | 0.987 |
| ISOBUTYRYLGLYCINE | yes | yes | *29.40%* | *27.00%* | *0.898* | 0.982 |
| UREA | yes | yes | 5.20% | 9.40% | 0.999 | 0.994 |
| STEAROYLCARNITINE | yes | yes | 8.60% | 7.20% | 0.997 | 0.999 |
| RICINOLEIC ACID | yes | yes | 6.50% | 15.60% | 0.983 | 0.93 |
| 13-OXOOCTADECANOIC ACID | yes | yes | 13.4% | 9.0% | 0.986 | 0.99 |
| 3-HYDROXYTETRADECANOIC ACID | yes | yes | 13.1% | 22.3% | *0.752* | *0.734* |
| 1-HEPTADECANOYL-2-HYDROXY-SN-GLYCERO-3-PHOSPHOCHOLINE | yes | yes | 6.40% | 11.50% | 0.994 | 0.975 |
| BILIRUBIN | yes | yes | 14.60% | 6.20% | 0.974 | 0.975 |
| BILIVERDIN | yes | yes | 16.90% | 12.00% | 0.943 | 0.859 |
| ETIOCHOLANOLONE GLUCURONIDE | yes | yes | 9.60% | 11.10% | 0.988 | 0.99 |
| COTININE | yes | yes | 3.60% | 6.70% | 0.997 | 0.99 |
| MYRISTIC ACID | yes | yes | 6.70% | 8.00% | 0.997 | 0.941 |
| STEARIC ACID | yes | yes | 17.00% | 15.20% | 0.967 | *0.876* |
| L-(+)-ERGOTHIONEINE | yes | yes | 14.10% | *25.40%* | 0.985 | 0.981 |
| 20-CARBOXY-LEUKOTRIENE B4 | yes | yes | 11.20% | 12.10% | *0.855* | *0.764* |
| 2-HYDROXYTETRADECANOIC ACID | yes | yes | 6.20% | 5.90% | 0.99 | 0.991 |
| 1-PALMITOYL-2-HYDROXY-SN-GLYCERO-3-PHOSPHOCHOLINE (LYSOPC(16:0)) | yes | yes | 6.10% | 8.00% | 0.997 | 0.999 |
| L-ACETYLCARNITINE | yes | yes | 5.10% | 4.70% | 0.999 | 0.998 |
| L-LYSINE | yes | yes | 5.30% | 8.90% | 0.993 | 0.959 |
| MIXTURE OF [L-GLUTAMINE & 2-METHYLGLUTARIC ACID] | yes | yes | 4.10% | 3.80% | 0.989 | 0.999 |

Chrom; poorly resolved from 2-Hydroxybutanoic acid;
*below detection limit for mass spectrometer used;
partial recovery with the "crash" formulation used, improved recoveries achievable with increasing the IPA fraction within the formulation;
⁺read-out is a combined signal of 1,3-rac-Dilinoleoyl-glycerol and 1,2-rac-Dilinoleoyl-glycerol In Table 6, the results for the extractability, precision and calibration assessments are summarized for the extractions using the proprietary "crash" formulation from blood specimens collected using volumetric Neoteryx Mitra microsampling devices as well as for comparator conventionally extracted EDTA plasma samples. Data in bold are considered of high quality (respectively, low imprecision % CV:515%, or $r^2>0.98$), whereas the italic values are considered of low quality (high imprecision % CV>25%, or $r^2<0.90$).

From Table 6, it can be concluded that the here disclosed proprietary "crash" enables for the effective and quantifiable extraction of metabolites of interest across all relevant metabolite classes from alternative collection media, and more specifically from DBS-technology type of sampling media.

Taken the exemplary but non-limiting extraction, imprecision and calibration data together, the data as shown here confirm that the novel formulation, "crash", as developed by the inventors, is suitable to extract metabolites of interest across metabolite classes with different physicochemical properties from different types of blood specimens, and from different specimen sampling media. This confirms this "crash" solvent, and, or derived compositions thereof, highly suited for the aims as laid out in this application, and more specifically for the implementation of prognostic tests, as disclosed elsewhere in this application in $1^{st}$ line clinical care.

Example 6: Dual Separation of Metabolites by Liquid Chromatography

Underpinning the collection of methods as laid out in this application, is the capability to unambiguously identify and quantify collections of blood-borne metabolites which are, on their own and/or as part of a combination of metabolites, relevant to the diagnosis or risk prediction of a (future) health outcome. To enable identification and quantification by mass spectrometry (Example 7), the metabolites of interest need to be sufficiently resolved from each other, i.e., separated, to allow for the mass spectrometer to perform accurate quantification. Key to this, is the need for appropriate cycle time, i.e., the mass spectrometer needs to be able to collect sufficient data points across a chromatographic peak to allow for correct integration, i.e., quantification, of these peaks. With lists of metabolites of interest often extensive and the need for co-analysis of SIL-IS warranted, the need for separation becomes apparent. In addition, the metabolites of interest should be delivered to the mass spectrometer in such a fashion that their ionization is facilitated, and at the same time, the delivery solvents should be compatible with mass spectrometric detection. Typically, but not limiting, ionization in electrospray ionization is favourable when the compounds of interest are delivered to the mass spectrometer in a solvent which has a significant organic content, as the latter are typically more volatile. This in turn will determine the optimal chromatographic procedure to be used to separate a metabolite of interest from others, in accordance with physicochemical properties of the metabolite of interest. Taking these prerequisites in account, and in view of the collection of methods disclosed here, the inventors established a dual chromatographic system for the blood-derived metabolite extracts.

Typically, but not limiting, 2 or more aliquots are generated as a result of the metabolite extraction work-up of the blood specimens. (cf. Example 2).

For each blood specimen, an aliquot will be subjected to an LC-MS/MS analysis combining C18 Reversed Phase Liquid Chromatography (RPLC) with MS/MS analysis (cf. Example 7). In this analysis, the hydrophobic metabolites of interest (and the associated SIL-IS) are analysed.

Then another aliquot, originating from the same blood specimen, will be subjected to an LC-MS/MS analysis combining Hydrophilic Interaction Liquid Chromatography (HILIC) with MS/MS analysis (cf. Example 7). In this analysis, the hydrophilic metabolites of interest (and the associated SIL-IS) are analysed.

Typical, but non-limiting examples of LC methods, are detailed below:

Materials and Reagents Used in the Dual Separations.

LC-MS grade ammonium acetate ($NH_4OAc$) and ammonium formate ($NH_4HCOO$) were purchased from Fluka (Arklow, Ireland). LC-MS optima grade acetic acid, acetonitrile (ACN), methanol (MeOH) and 2-Propanol (IPA) were purchased from Fischer scientific (Blanchardstown, Ireland). Metabolite reference substances and Stable Isotope labelled (SIL) standards are as presented in Table 7 and 8.

For the RPLC, the column-type used was a Zorbax Eclipse Plus C18 Rapid Resolution HD 2.1×50 mm, 1.8-Micron column (P.N. 959757-902; Agilent Technologies, Little Island, Ireland). For the HILIC-MS/MS, the column type was an Ascentis Express HILIC 150×2.1 mm, 2.7 Micron (P.N. 53946-U: Sigma-Aldrich, Arklow, Ireland) Instrument: The LC-MS/MS platform used consisted of a 1260 Infinity LC system (Agilent Technologies, Waldbronn, Germany). The latter was coupled to an Agilent Triple Quadrupole 6460 mass spectrometer (QqQ-MS) equipped with an JetStream Electrospray Ionisation source (Agilent Technologies, Santa Clara, CA, USA) (Cf. Example 6).

RPLC:

The RPLC method is defined by the following settings/parameters:

Injection volume: 7 μL

Column oven temperature: 60° C.

Gradient RPLC was performed to resolve the hydrophobic metabolites using a binary solvent system:

mobile phase A: Water:MeOH:$NH_4OAc$ buffer 200 mM at pH 4.5, (92:3:5)

mobile phase B: MeOH:Acetonitrile:IPA:$NH_4OAc$ 200 mM at pH 4.5 (35:35:25:5) A linear gradient program was applied: from 10% mobile phase B to 100% mobile phase B in 10 minutes, using the following gradient—flow rate program:

| Time (min) | Mobile A phase | Mobile phase B | Flow rate (mL/min) |
|---|---|---|---|
| 0.00 | 100% | 0% | 0.35 |
| 6.00 | 0% | 100% | 0.50 |
| 8.00 | 0% | 100% | 0.50 |
| 8.10 | 100% | 0% | 0.50 |
| 9.00 | 100% | 0% | 0.50 |
| 10.00 | 100% | 0% | 0.350 |

Using this chromatographic method, the hydrophobic metabolites of interest and corresponding SIL-IS were characterized by the following retention times, detailed in Table 7

Please note: Not all the metabolites of interest have an according SIL-IS available.

The efflux of the RPLC column was led directly to the QqQ-MS for mass spectrometric determination of the hydrophobic compounds of interest (Example 7).

TABLE 7

Exemplary retention times for hydrophobic metabolites of interest and SIL-IS

| Metabolite | | SIL-IS | |
| --- | --- | --- | --- |
| Name | Rt (min) | Name | Rt (min) |
| 25-Hydroxyvitamin $D_3$ | 6.600 | 25-Hydroxyvitamin D3-[$^2H_3$] | 6.608 |
| Arachidonic acid | 6.812 | Arachidonic acid-[$^2H_8$] | 6.797 |
| 8,11,14 Eicosatrienoic acid | 6.963 | Arachidonic acid-[$^2H_8$] | 6.797 |
| Decanoylcarnitine | 4.738 | Decanoylcarnitine-[$^2H_3$] | 4.723 |
| Dodecanoyl-L-carnitine (C12) | 5.400 | Dodecanoyl-l-carnitine-[$^2H_3$] | 5.400 |
| Docosahexaenoic acid | 6.751 | Docsaohexaenoic acid-[$^2H_5$] | 6.736 |
| Dilinoleoyl-glycerol[+] | 8.800 | 1,3-Dilinoleoyl-rac-glycerol-[$^2H_5$] | 8.800 |
| Hexadecanoic acid | 7.026 | Hexadecanoic acid-[$^2H_4$] | 7.026 |
| Linoleic acid | 6.860 | Linoleic acid-[$^{13}C_{18}$] | 6.860 |
| Oleic acid | 7.101 | Oleic acid-[$^{13}C_5$] | 7.101 |
| L-Palmitoylcarnitine | 6.323 | Palmitoyl carnitine-[$^2H_3$] | 6.322 |
| Sphingosine 1-phosphate | 6.128 | Sphingosine-1-phosphate-[$^{13}C_2$, $^2H_2$] | 6.127 |
| Sphinganine-1-phosphate (C18 base) | 6.248 | Sphingosine-1-phosphate-[$^{13}C_2$, $^2H_2$] | 6.127 |
| Stearoylcarnitine | 6.729 | Stearoyl-L-carnitine [$^2H_3$] | 6.729 |
| Eicosapentaenoic acid | 6.620 | Hexadecanoic acid-[$^2H_4$] | 7.026 |
| Ricinoleic acid | 6.057 | Linoleic acid-[$^{13}C_{18}$] | 6.860 |
| 13-Oxooctadecanoic acid | 6.300 | Linoleic acid-[$^{13}C_{18}$] | 6.860 |
| 3-Hydroxytetradecanoic acid | 5.801 | Linoleic acid-[$^{13}C_{18}$] | 6.860 |
| Bilirubin | 6.501 | Bilirubin [$^2H_4$] | 6.485 |
| Biliverdin | 5.126 | Biliverdin [$^2H_4$] | 5.065 |
| Etiocholanolone glucuronide | 7.098 | Oleic acid- [$^{13}C_5$] | 7.101 |
| Myristic acid | 6.650 | Docosahexaenoic acid-[$^2H_5$] | 6.736 |
| Stearic acid | 7.358 | Linoleic acid-[$^{13}C_{18}$] | 6.860 |
| 1-oleoyl-2-hydroxy-sn-glycero-3-phospho-L-serine | 6.350 | Linoleic acid-[$^{13}C_{18}$] | 6.860 |
| 20-Carboxy-leukotriene B4 | 7.355 | Docosahexaenoic acid-[$^2H_5$] | 6.736 |
| 2-Hydroxytetradecanoic acid | 5.800 | Docosahexaenoic acid-[$^2H_5$] | 6.736 |
| 1-Palmitoyl-2-hydroxy-sn-glycero-3-phosphocholine (LysoPC(16:0)) | 6.457 | Linoleic acid-[$^{13}C_{18}$] | 6.860 |
| 6-Hydroxysphingosine | 5.630 | Sphingosine-1-phosphate-[$^{13}C_2$, $^2H_2$] | 6.127 |
| Sphinganine-1-phosphate (C17 base) | 6.022 | Sphingosine-1-phosphate-[$^{13}C_2$, $^2H_2$] | 6.127 |

[+]read-out is a combined signal of 1,3-rac-Dilinoleoyl-glycerol and 1,2-rac-Dilinoleoyl-glycerol HILIC:
The HILIC method is defined by the following settings/parameters:
Injection volume: 3 µL, whereby the injection plug was bracketed by 3 µL ACN solvent plugs; a specific injector program was devised for this.
Column oven temperature: 30° C.
Gradient HILIC was performed to resolve the hydrophobic metabolites using a binary solvent system:
mobile phase A: 50 mM Ammonium formate (aqueous)
mobile phase B: ACN
A linear step gradient program was applied: from 10% mobile phase B to 100% mobile phase B in 10 minutes. using the following gradient—flow rate program:

| Time (min) | Mobile phase A | Mobile phase B | Flow rate (mL/min) |
| --- | --- | --- | --- |
| 0.00 | 12% | 88% | 0.45 |
| 1.10 | 20% | 80% | 0.45 |
| 2.00 | 20% | 80% | 0.45 |
| 2.10 | 30% | 70% | 0.45 |
| 3.00 | 30% | 70% | 0.45 |
| 3.10 | 40% | 60% | 0.45 |
| 4.00 | 40% | 60% | 0.45 |
| 6.00 | 50% | 50% | 0.45 |
| 7.20 | 50% | 50% | 0.45 |
| 7.21 | 12% | 88% | 0.45 |
| 10.00 | 12% | 88% | 0.45 |

Using this chromatographic method, the hydrophilic metabolites of interest and corresponding SIL-IS were characterized by the following retention times; Table 8. Please note: Not all of the metabolites of interest have an according SIL-IS available.

The efflux of the HILIC column was led directly to the QqQ-MS for mass spectrometric determination of the hydrophobic compounds of interest (Example 7).

TABLE 8

Exemplary retention times for hydrophilic metabolites of interest and SIL-IS

| Metabolite | | ISTD | |
| --- | --- | --- | --- |
| Name | Rt (min) | Name | Rt (min) |
| 2-Hydroxybutanoic acid | 2.263 | 2-Hydroxybutyrate [$^2H_3$] | 2.249 |
| 3-Hydroxybutanoic acid | 2.683 | 3-Hydroxybutanoic acid [$^2H_4$] | 2.710 |
| Adipic acid | 5.058 | Adipic acid [$^2H_4$] | 4.777 |

TABLE 8-continued

Exemplary retention times for hydrophilic metabolites of interest and SIL-IS

| Metabolite | | ISTD | |
|---|---|---|---|
| Name | Rt (min) | Name | Rt (min) |
| L-Alanine | 4.552 | L-Alanine-[$^{13}C_3$] | 4.552 |
| L-Arginine | 6.814 | L-Arginine-[$^{13}C_6$] | 6.813 |
| L-Leucine | 3.400 | Leucine-[$^{13}C_6$] | 3.445 |
| Citrulline | 5.038 | L-citrulline [$^2H_7$] | 5.051 |
| Choline | 5.684 | Choline-[$^2H_9$] | 5.684 |
| Glycyl-glycine | 5.417 | Glycyl-glycine [$^{13}C_4$, $^{15}N_2$] | 5.417 |
| Homo-L-arginine | 6.784 | Homo-L-arginine [$^{13}C_7$, $^{15}N_4$] | 6.784 |
| L-Isoleucine | 3.600 | Isoleucine-[$^{13}C_6$] | 3.599 |
| L-Methionine | 3.542 | L-Methionine-[$^{13}C_5$] | 3.542 |
| NG-Monomethyl-L-arginine | 7.218 | Homo-L-arginine [$^{13}C_7$, $^{15}N_4$] | |
| Asymmetric dimethylarginine | 7.888 | Asymmetric dimethyl arginine [$^2H_6$] | 7.901 |
| Symmetric dimethylarginine | 7.650 | Symmetric dimethylarginine- [$^2H_6$] | 7.650 |
| Taurine | 2.859 | Taurine [$^{13}C_2$] | 2.873 |
| Isobutyrylglycine | 3.000 | N-Isobutyryiglycine [$^{13}C_2$, $^{15}N$] | 3.025 |
| Urea | 1.267 | Urea [$^{13}C$, $^{18}O$] | 1.281 |
| Cotinine | 1.346 | (±)-Cotinine [$^2H_3$] | 1.360 |
| L-(+)-Ergothioneine | 4.797 | L-(+)-Ergothioneine [$^2H_9$] | 4.797 |
| L-Acetylcarnitine | 6.112 | L-Acetylcarnitine [$^2H_3$] | 6.112 |
| L-Lysine | 7.388 | L-Acetylcarnitine [$^2H_3$] | 6.112 |
| Mixture of [2-methylglutaric acid and L-Glutamine] | 4.751 | L-Glutamine [$^{13}C_5$] | 4.749 |

Example 7: Tandem MS/MS

Tandem mass spectroscopy was carried out under both positive and negative electrospray ionization and multiple reaction monitoring (MRM) mode. For each metabolite of interest, the following parameters were specifically established and optimized for each and every metabolite of interest and each SIL-IS available:
- appropriate precursor ion m/z, inclusive its preferred ionization mode (positive or negative),
- Product ion spectra under various collision voltage conditions (cf. induction of ion-molecule collisions under different energy regimens, leading to specific product ions) and selection of the most appropriate Quantifier and Qualifier product ions to be used for mass spectrometric identification and quantifications.
- Establishment of the reference Quantifier ion/Qualification ion ratios which to serve for specificity assessment.
- In addition, a number of assay specific instrument parameters were also optimized per compound of interest: quadrupole resolutions, dwell time, fragmentor voltage, collision energy and cell Aaccelerator Vvoltage.

At the same time, instrument-specific parameters were optimised to maximally maintain compound integrity in the electrospray source and achieve sensitive and specific metabolite analysis; source temperature, sheath gas flow, drying gas flow and capillary voltage.

Instrument: The LC-MS/MS platform used consisted of a 1260 Infinity LC system (Agilent Technologies, Waldbronn, Germany) was coupled to an Agilent Triple Quadrupole 6460 mass spectrometer (QqQ-MS) equipped with an Jet-Stream Electrospray Ionisation source (Agilent Technologies, Santa Clara, CA, USA).

RPLC-ESI-MS/MS

For the mass spectrometric method used for analysing the hydrophobic metabolites of interest, the optimized electrospray ionization source parameters are as follows:

| Source Parameters | Positive mode | Negative mode |
|---|---|---|
| Gas Temperature, ° C. | 200 | 200 |
| Gas flow, L/min | 13 | 13 |
| Nebuliser, psi | 40 | 40 |
| Sheath Gas Heater, ° C. | 400 | 400 |
| Sheath Gas Flow, L/min | 11 | 11 |
| Capillary, V | 5000 | 3000 |
| V Charging | 300 | 300 |

The MRM parameters established to enable unambiguous identification of the hydrophobic metabolites of interest and according SIL-IS are presented in Table 9.

TABLE 9

MRM parameters for the hydrophobic metabolites of interest and associated SIL-IS

| Metabolite | Quant/ Qual | MS1 m/z (Res) | MS2 m/z (Res) | Quant/ Qual ratio | Dwell (ms) | Frag (V) | CE (V) | CAV (V) | Polarity |
|---|---|---|---|---|---|---|---|---|---|
| 25-Hydroxyvitamin D3 | Quant | 401.3 (Wide) | 383.3 (Wide) | 23.6 | 20 | 104 | 4 | 2 | Positive |
| | Qual | 401.3 (Wide) | 365.3 (Wide) | | 20 | 104 | 4 | 2 | Positive |
| Arachidonic acid | Quant | 303.1 (Unit) | 259.1 (Unit) | 34.7 | 3 | 135 | 3 | 2 | Negative |
| | Qual | 303.1 (Unit) | 59.1 (Unit) | | 3 | 135 | 15 | 2 | Negative |
| 8,11,14 Eicosatrienoic acid | Quant | 305.1 (Unit) | 305.0 (Unit) | 152.7 | 3 | 80 | 1 | 2 | Negative |
| | Qual | 305.1 (Unit) | 304.9 (Unit) | | 3 | 80 | 0 | 2 | Negative |
| Decanoylcarnitine | Quant | 316.1 (Unit) | 60.1 (Unit) | 59.9 | 3 | 190 | 24 | 2 | Positive |
| | Qual | 316.1 (Unit) | 257.1 (Unit) | | 3 | 190 | 12 | 2 | Positive |
| Dodecanoyl-l-carnitine (C12) | Quant | 344.1 (Unit) | 85.1 (Unit) | 37.8 | 3 | 140 | 21 | 3 | Positive |
| | Qual | 344.1 (Unit) | 85.0 (Unit) | | 3 | 140 | 51 | 3 | Positive |
| Docosahexaenoic | Quant | 327.1 (Unit) | 283.1 (Unit) | 11.8 | 3 | 80 | 5 | 2 | Negative |

TABLE 9-continued

MRM parameters for the hydrophobic metabolites of interest and associated SIL-IS

| Metabolite | Quant/Qual | MS1 m/z (Res) | MS2 m/z (Res) | Quant/Qual ratio | Dwell (ms) | Frag (V) | CE (V) | CAV (V) | Polarity |
|---|---|---|---|---|---|---|---|---|---|
| acid | Qual | 327.1 (Unit) | 229.1 (Unit) | | 3 | 80 | 5 | 2 | Negative |
| Dilinoleoyl- | Quant | 634.4 (Unit) | 337.5 (Unit) | 185.4 | 3 | 84 | 28 | 2 | Positive |
| glycerol+ | Qual | 634.4 (Unit) | 599.2 (Unit) | | 3 | 84 | 16 | 2 | Positive |
| Hexadecanoic | Quant | 255.1 (Unit) | 255.1 (Unit) | 21.5 | 3 | 130 | 15 | 3 | Negative |
| acid | Qual | 255.1 (Unit) | 255.0 (Unit) | | 3 | 130 | 20 | 3 | Negative |
| Linoleic acid | Quant | 279.1 (Unit) | 279.1 (Unit) | 13.8 | 3 | 104 | 10 | 2 | Negative |
| | Qual | 279.1 (Unit) | 279.0 (Unit) | | 3 | 104 | 20 | 2 | Negative |
| Oleic acid | Quant | 281.1 (Unit) | 281.1 (Unit) | 22.3 | 3 | 128 | 10 | 3 | Negative |
| | Qual | 281.1 (Unit) | 281.0 (Unit) | | 3 | 128 | 20 | 3 | Negative |
| L- | Quant | 400.2 (Unit) | 60.2 (Unit) | 34.8 | 3 | 110 | 26 | 2 | Positive |
| Palmitoylcarnitine | Qual | 400.2 (Unit) | 341.2 (Unit) | | 3 | 110 | 17 | 2 | Positive |
| Sphingosine-1- | Quant | 380.1 (Unit) | 264.2 (Unit) | 5.9 | 3 | 100 | 11 | 3 | Positive |
| phosphate | Qual | 380.1 (Unit) | 362.2 (Unit) | | 3 | 100 | 11 | 3 | Positive |
| Sphinganine-1 | Quant | 382.0 (Unit) | 284.0 (Unit) | 43.3 | 3 | 100 | 8 | 3 | Positive |
| phosphate (C18 base) | Qual | 382.0 (Unit) | 266.0 (Unit) | | 3 | 100 | 12 | 3 | Positive |
| Stearoylcarnitine | Quant | 428.3 (Unit) | 85.0 (Unit) | 2.7 | 3 | 130 | 25 | 5 | Positive |
| | Qual | 428.3 (Unit) | 369.3 (Unit) | | 3 | 130 | 15 | 5 | Positive |
| Eicosapentaenoic | Quant | 301.1 (Unit) | 257.0 (Unit) | 15.1 | 3 | 120 | 5 | 5 | Negative |
| acid | Qual | 301.1 (Unit) | 59.2 (Unit) | | 3 | 120 | 15 | 5 | Negative |
| Ricinoleic acid | Quant | 297.2 (Unit) | 183.1 (Unit) | 24.7 | 3 | 120 | 15 | 7 | Negative |
| | Qual | 297.2 (Unit) | 279.0 (Unit) | | 3 | 120 | 10 | 7 | Negative |
| 13-Oxooctadecanoic | Quant | 299.4 (Unit) | 281.2 (Unit) | 12.5 | 3 | 100 | 5 | 4 | Positive |
| acid | Qual | 299.4 (Unit) | 111.2 (Unit) | | 3 | 100 | 10 | 4 | Positive |
| 3-Hydroxytetradecanoic | Quant | 243.1 (Unit) | 59.1 (Unit) | 2.5 | 3 | 120 | 2 | 2 | Negative |
| acid | Qual | 243.1 (Unit) | 41.1 (Unit) | | 3 | 120 | 45 | 2 | Negative |
| Bilirubin | Quant | 585.2 (Unit) | 299.1 (Unit) | 0.7 | 3 | 125 | 20 | 5 | Positive |
| | Qual | 585.2 (Unit) | 213.1 (Unit) | | 3 | 125 | 45 | 3 | Positive |
| Biliverdin | Quant | 583.2 (Unit) | 297.1 (Unit) | 200.7 | 3 | 135 | 35 | 5 | Positive |
| | Qual | 583.2 (Unit) | 583.1 (Unit) | | 3 | 135 | 0 | 5 | Positive |
| Etiocholanolone | Quant | 465.2 (Unit) | 465.1 (Unit) | Na | 3 | 135 | 0 | 6 | Negative |
| glucuronide | Qual | 465.2 (Unit) | 113.0 (Unit) | | 3 | 135 | 35 | 6 | Negative |
| Myristic acid | Quant | 227.2 (Unit) | 227.1 (Unit) | 0.5 | 3 | 145 | 0 | 4 | Negative |
| | Qual | 227.2 (Unit) | 53.8 (Unit) | | 3 | 145 | 45 | 4 | Negative |
| Stearic acid | Quant | 283.2 (Unit) | 265.0 (Unit) | 6.8 | 3 | 145 | 19 | 2 | Negative |
| | Qual | 283.2 (Unit) | 45.1 (Unit) | | 3 | 145 | 20 | 2 | Negative |
| 1-oleoyl-2-hydroxy- | Quant | 524.4 (Unit) | 339.1 (Unit) | 23.6 | 3 | 120 | 20 | 4 | Positive |
| sn-glycero-3-phospho-L-serine | Qual | 524.4 (Unit) | 506.2 (Unit) | | 3 | 120 | 10 | 4 | Positive |
| 20-Carboxy- | Quant | 365.0 (Unit) | 364.9 (Unit) | 0.5 | 3 | 120 | 0 | 5 | Negative |
| leukotriene B4 | Qual | 365.0 (Unit) | 195.0 (Unit) | | 3 | 120 | 15 | 5 | Negative |
| 2-Hydroxytetradecanoic | Quant | 243.1 (Unit) | 197.2 (Unit) | 374.6 | 3 | 120 | 15 | 2 | Negative |
| acid | Qual | 243.1 (Unit) | 243.0 (Unit) | | 3 | 120 | 0 | 2 | Negative |
| 1-Palmitoyl-2- hydroxy-sn- | Quant | 496.2 (Unit) | 104.1 (Unit) | 34.3 | 3 | 120 | 10 | 2 | Positive |
| glycero-3-phosphocholine (LysoPC(16:0)) | Qual | 496.2 (Unit) | 184.0 (Unit) | | 3 | 120 | 5 | 2 | Positive |
| 6-Hydroxysphingosine | Quant | 316.2 (Unit) | 60.1 (Unit) | 12.3 | 3 | 100 | 10 | 7 | Positive |
| | Qual | 316.2 (Unit) | 280.1 (Unit) | | 3 | 100 | 10 | 7 | Positive |
| Sphinganine-1- | Quant | 368.1 (Unit) | 270.0 (Unit) | 16.7 | 3 | 100 | 10 | 4 | Positive |
| phosphate (C17 base) | Qual | 368.1 (Unit) | 252.0 (Unit) | | 3 | 100 | 25 | 4 | Positive |
| SIL-IS | | | | | | | | | |
| 25-Hydroxyvitamin | Quant | 404.2 (Wide) | 386.2 (Wide) | 46.6 | 20 | 98 | 10 | 2 | Positive |
| $D_3$-$[^2H_3]$ | Qual | 404.2 (Wide) | 368.3 (Wide) | | 20 | 98 | 10 | 2 | Positive |
| Arachidonic acid-$[^2H_8]$ | Quant | 311.1 (Unit) | 267.1 (Unit) | 36.1 | 3 | 135 | 3 | 2 | Negative |
| | Qual | 311.1 (Unit) | 59.1 (Unit) | | 3 | 135 | 15 | 3 | Negative |
| Decanoylcarnitine-$[^2H_3]$ | Quant | 319.1 (Unit) | 63.1 (Unit) | 46.6 | 3 | 190 | 24 | 2 | Positive |
| | Qual | 319.1 (Unit) | 257.1 (Unit) | | 3 | 190 | 12 | 2 | Positive |
| Dodecanoyl-l-carnitine-$[^2H_3]$ | Quant | 347.1 (Unit) | 85.1 (Unit) | 29.8 | 3 | 140 | 21 | 3 | Positive |
| | Qual | 347.1 (Unit) | 85.0 (Unit) | | 3 | 140 | 51 | 3 | Positive |
| Docosahexaenoic | Quant | 332.1 (Unit) | 288.1 (Unit) | 12.1 | 3 | 80 | 5 | 2 | Negative |
| acid-$[^2H_5]$ | Qual | 332.1 (Unit) | 234.1 (Unit) | | 3 | 80 | 5 | 2 | Negative |
| 1,3-Dilinoleoyl-rac- | Quant | 639.4 (Unit) | 342.5 (Unit) | 141.1 | 3 | 84 | 20 | 2 | Positive |
| glycerol-$[^2H_5]$ | Qual | 639.4 (Unit) | 604.2 (Unit) | | 3 | 04 | 10 | 2 | Positive |
| Hexadecanoic acid-$[^2H_4]$ | Quant | 259.1 (Unit) | 259.1 (Unit) | 24.1 | 3 | 130 | 15 | 3 | Negative |
| | Qual | 259.1 (Unit) | 259.0 (Unit) | | 3 | 130 | 20 | 3 | Negative |
| Linoleic acid-$[^{13}C_{18}]$ | Quant | 297.3 (Unit) | 297.3 (Unit) | 21.5 | 3 | 104 | 10 | 3 | Negative |
| | Qual | 297.3 (Unit) | 297.2 (Unit) | | 3 | 104 | 20 | 3 | Negative |
| Oleic acid-$[^{13}C_5]$ | Quant | 286.3 (Unit) | 286.3 (Unit) | 24.5 | 3 | 128 | 10 | 3 | Negative |
| | Qual | 286.3 (Unit) | 286.2 (Unit) | | 3 | 128 | 20 | 3 | Negative |
| Palmitoyl carnitine-$[^2H_3]$ | Quant | 403.2 (Unit) | 63.2 (Unit) | 29.7 | 3 | 190 | 5 | 2 | Positive |
| | Qual | 403.2 (Unit) | 341.2 (Unit) | | 3 | 190 | 0 | 2 | Positive |
| Sphingosine-1-phosphate-$[^{13}C_2,^2H_2]$ | Quant | 384.2 (Unit) | 268.2 (Unit) | 4.3 | 3 | 100 | 11 | 3 | Positive |
| | Qual | 384.2 (Unit) | 366.2 (Unit) | | 3 | 100 | 11 | 3 | Positive |

TABLE 9-continued

MRM parameters for the hydrophobic metabolites of interest and associated SIL-IS

| Metabolite | Quant/ Qual | MS1 m/z (Res) | MS2 m/z (Res) | Quant/ Qual ratio | Dwell (ms) | Frag (V) | CE (V) | CAV (V) | Polarity |
|---|---|---|---|---|---|---|---|---|---|
| Stearoyl-L-carnitine [$^2$H$_3$] | Quant | 431.3 (Unit) | 85.0 (Unit) | 2.7 | 3 | 130 | 25 | 5 | Positive |
| | Qual | 431.3 (Unit) | 369.3 (Unit) | | 3 | 130 | 15 | 5 | Positive |
| Bilirubin [$^2$H$_4$] | Quant | 590.2 (Unit) | 301.2 (Unit) | 98.8 | 3 | 125 | 15 | 5 | Positive |
| | Qual | 590.2 (Unit) | 303.2 (Unit) | | 3 | 125 | 15 | 5 | Positive |
| Biliverdin ($^2$H$_4$) | Quant | 586.0 (Unit) | 299.2 (Unit) | NA | 3 | 130 | 35 | 5 | Positive |

+read-out is a combined signal of 1,3-rac-Dilinoleoyl-glycerol and 1,2-rac-Dilinoleoyl-glycerol

HILIC-MS/MS:

For the mass spectrometric method used for analysing the hydrophilic metabolites of interest, the optimized electrospray ionization source parameters are as follows:

| Parameters | Positive mode | Negative mode |
|---|---|---|
| Gas Temperature, ° C. | 200 | 200 |
| Gas flow, L/min | 13 | 13 |
| Nebuliser, psi | 40 | 40 |
| Sheath Gas Heater, ° C. | 400 | 400 |
| Sheath Gas Flow, L/min | 12 | 12 |
| Capillary, V | 2500 | 3000 |
| V Charging | 300 | 300 |

The MRM parameters established to enable unambiguous identification of the hydrophilic metabolites of interest and according SIL-IS are presented in Table 10.

TABLE 10

MRM parameters for the hydrophilic metabolites of interest and associated SIL-IS

| Metabolite | Quant/ Qual | MS1 Res | MS2 Res | Quant/ Qual ratio | Dwell (ms) | Frag (V) | CE (V) | CAV (V) | Polarity |
|---|---|---|---|---|---|---|---|---|---|
| 2-Hydroxybutanoic acid | Quant | 103.0 (Unit) | 57.2 (Unit) | 14.0 | 15 | 84 | 8 | 4 | Negative |
| | Qual | 103.0 (Unit) | 45.2 (Unit) | | 15 | 84 | 5 | 4 | Negative |
| Mixture of [L-Glutamine & 2-Methylglutaric acid] | Quant | 145.0 (Unit) | 101.2 (Unit) | 9.4 | 15 | 80 | 8 | 4 | Negative |
| | Qual | 145.0 (Unit) | 83.2 (Unit) | | 15 | 80 | 12 | 4 | Negative |
| | Quant# | 101.1 (Unit) | 101.2 (Unit) | 179.1 | 3 | 120 | 2 | 5 | Negative |
| | Qual# | 101.1 (Unit) | 101.0 (Unit) | | 3 | 120 | 0 | 5 | Negative |
| 3-Hydroxybutanoic acid | Quant | 103.1 (Unit) | 59.1 (Unit) | 344.9 | 15 | 78 | 8 | 4 | Negative |
| | Qual | 103.1 (Unit) | 103.1 (Unit) | | 15 | 78 | 0 | 4 | Negative |
| Adipic acid | Quant | 145.1 (Unit) | 83.2 (Unit) | 221.7 | 3 | 80 | 12 | 4 | Negative |
| | Qual | 145.1 (Unit) | 101.2 (Unit) | | 3 | 80 | 8 | 4 | Negative |
| L-Alanine | Quant | 90.1 (Unit) | 90.1 (Unit) | 74.7 | 3 | 62 | 0 | 2 | Positive |
| | Qual | 90.1 (Unit) | 44.11 (Unit) | | 3 | 62 | 8 | 2 | Positive |
| L-Arginine | Quant | 175.0 (Unit) | 116.0 (Unit) | 505.9 | 3 | 82 | 15 | 2 | Positive |
| | Qual | 175.0 (Unit) | 70.1 (Unit) | | 3 | 82 | 20 | 2 | Positive |
| L-Leucine | Quant | 132.0 (Unit) | 86.2 (Unit) | 19.6 | 3 | 104 | 10 | 4 | Positive |
| | Qual | 132.0 (Unit) | 44.2 (Unit) | | 3 | 104 | 25 | 4 | Positive |
| Citrulline | Quant | 176.0 (Unit) | 113.0 (Unit) | 261.2 | 3 | 68 | 15 | 5 | Positive |
| | Qual | 176.0 (Unit) | 70.1 (Unit) | | 3 | 68 | 20 | 5 | Positive |
| Choline | Quant | 104.1 (Unit) | 45.3 (Unit) | 171.5 | 3 | 40 | 27 | 2 | Positive |
| | Qual | 104.1 (Unit) | 60.3 (Unit) | | 3 | 40 | 17 | 2 | Positive |
| Glycyl-glycine | Quant | 133.1 (Unit) | 30.4 (Unit) | 15.7 | 3 | 58 | 20 | 4 | Positive |
| | Qual | 133.1 (Unit) | 76.2 (Unit) | | 3 | 58 | 5 | 4 | Positive |
| Homo-L-arginine | Quant | 189.0 (Unit) | 144.2 (Unit) | 2.6 | 3 | 88 | 15 | 2 | Positive |
| | Qual | 189.0 (Unit) | 57.1 (Unit) | | 3 | 88 | 25 | 2 | Positive |
| L-Isoleucine | Quant | 132.0 (Unit) | 69.2 (Unit) | 22.9 | 3 | 104 | 19 | 2 | Positive |
| | Qual | 132.0 (Unit) | 57.2 (Unit) | | 3 | 104 | 32 | 2 | Positive |
| L-Methionine | Quant | 150.0 (Unit) | 56.2 (Unit) | 37.0 | 3 | 104 | 16 | 2 | Positive |
| | Qual | 150.0 (Unit) | 104.1 (Unit) | | 3 | 104 | 14 | 2 | Positive |
| NG-Monomethyl-L-arginine | Quant | 189.0 (Unit) | 116.2 (Unit) | 180.2 | 3 | 88 | 15 | 2 | Positive |
| | Qual | 189.0 (Unit) | 70.2 (Unit) | | 3 | 88 | 15 | 2 | Positive |
| Asymmetric dimethylarginine | Quant | 203.0 (Unit) | 46.2 (Unit) | 188.5 | 3 | 100 | 15 | 4 | Positive |
| | Qual | 203.0 (Unit) | 70.1 (Unit) | | 3 | 100 | 18 | 4 | Positive |
| Symmetric dimethylarginine | Quant | 203.1 (Unit) | 172.2 (Unit) | 49.3 | 3 | 90 | 10 | 4 | Positive |
| | Qual | 203.1 (Unit) | 133.0 (Unit) | | 3 | 90 | 6 | 4 | Positive |
| Taurine | Quant | 126.1 (Unit) | 44.2 (Unit) | 35.7 | 3 | 100 | 20 | 2 | Positive |
| | Qual | 126.1 (Unit) | 108.0 (Unit) | | 3 | 100 | 10 | 2 | Positive |
| Isobutyrylglycine | Quant | 146.0 (Unit) | 76.2 (Unit) | 136.7 | 3 | 60 | 5 | 7 | Positive |
| | Qual | 146.0 (Unit) | 43.2 (Unit) | | 3 | 60 | 15 | 7 | Positive |
| Urea | Quant | 61.2 (Unit) | 44.3 (Unit) | 167.3 | 3 | 100 | 10 | 2 | Positive |
| | Qual | 61.2 (Unit) | 61.2 (Unit) | | 3 | 100 | 10 | 2 | Positive |
| Cotinine | Quant | 177.0 (Unit) | 80.0 (Unit) | 19.7 | 3 | 100 | 25 | 5 | Positive |
| | Qual | 177.0 (Unit) | 98.1 (Unit) | | 3 | 100 | 20 | 5 | Positive |
| L-(+)-Ergothioneine | Quant | 230.1 (Unit) | 127.0 (Unit) | 47.3 | 3 | 100 | 25 | 2 | Positive |
| | Qual | 230.1 (Unit) | 186.0 (Unit) | | 3 | 100 | 15 | 2 | Positive |

TABLE 10-continued

MRM parameters for the hydrophilic metabolites of interest and associated SIL-IS

| Metabolite | Quant/Qual | MS1 Res | MS2 Res | Quant/Qual ratio | Dwell (ms) | Frag (V) | CE (V) | CAV (V) | Polarity |
|---|---|---|---|---|---|---|---|---|---|
| L-Acetylcarnitine | Quant | 204.2 (Unit) | 60.1 (Unit) | 377.5 | 3 | 100 | 15 | 4 | Positive |
|  | Qual | 204.2 (Unit) | 85.0 (Unit) |  | 3 | 100 | 15 | 4 | Positive |
| L-Lysine | Quant | 146.9 (Unit) | 130.2 (Unit) | 613.4 | 1 | 100 | 20 | 2 | Positive |
|  | Qual | 146.9 (Unit) | 84.2 (Unit) |  | 1 | 100 | 2 | 2 | Positive |
| L-Glutamine | Quant | 144.9 (Unit) | 127.0 (Unit) | 31.8 | 3 | 100 | 10 | 2 | Negative |
|  | Qual | 144.9 (Unit) | 108.8 (Unit) |  | 3 | 100 | 15 | 2 | Negative |
| SIL-IS | | | | | | | | | |
| 2-Hydroxybutyrate-[$^2$H$^3$] | Quant | 106.0 (Unit) | 59.2 (Unit) | 12.9 | 15 | 84 | 8 | 4 | Negative |
|  | Qual | 106.0 (Unit) | 45.2 (Unit) |  | 15 | 84 | 5 | 4 | Negative |
| 2-Methylglutaric acid [$^{13}$C$_2$] | Quant | 147.0 (Unit) | 102.0 (Unit) | 24.8 | 15 | 80 | 10 | 4 | Negative |
|  | Qual | 147.0 (Unit) | 84.0 (Unit) |  | 15 | 80 | 10 | 4 | Negative |
| 3-Hydroxybutanoic acid [$^2$H$_4$] | Quant | 107.0 (Unit) | 107.0 (Unit) | 26.7 | 15 | 78 | 0 | 3 | Negative |
|  | Qual | 107.0 (Unit) | 59.1 (Unit) |  | 15 | 78 | 8 | 3 | Negative |
| Adipic acid [$^2$H$_4$] | Quant | 149.0 (Unit) | 105.2 (Unit) | 0.25 | 3 | 80 | 10 | 4 | Negative |
|  | Qual | 149.0 (Unit) | 87.2 (Unit) |  | 3 | 80 | 10 | 4 | Negative |
| L-Alanine-[$^{13}$C$_3$] | Quant | 93.1 (Unit) | 93.1 (Unit) | 94.5 | 3 | 62 | 0 | 2 | Positive |
|  | Qual | 93.1 (Unit) | 46.1 (Unit) |  | 3 | 62 | 8 | 2 | Positive |
| L-Arginine-[$^{13}$C$_6$] | Quant | 181.2 (Unit) | 61.3 (Unit) | 55.6 | 3 | 82 | 12 | 2 | Positive |
|  | Qual | 181.2 (Unit) | 121.1 (Unit) |  | 3 | 82 | 12 | 2 | Positive |
| Leucine-[$^{13}$C$_6$] | Quant | 138.0 (Unit) | 46.2 (Unit) | 10.7 | 3 | 104 | 25 | 4 | Positive |
|  | Qual | 138.0 (Unit) | 44.2 (Unit) |  | 3 | 104 | 25 | 4 | Positive |
| L-Citrulline [$^2$H$_7$] | Quant | 183.1 (Unit) | 120.1 (Unit) | 231.6 | 3 | 68 | 16 | 5 | Positive |
|  | Qual | 183.1 (Unit) | 166.1 (Unit) |  | 3 | 68 | 4 | 5 | Positive |
| Choline-[$^2$H$_9$] | Quant | 114.0 (Unit) | 45.2 (Unit) | 141.3 | 3 | 40 | 20 | 2 | Positive |
|  | Qual | 114.0 (Unit) | 69.2 (Unit) |  | 3 | 40 | 20 | 2 | Positive |
| Glycyl-giyclne [$^{13}$C$_4$, $^{15}$N$_2$] | Quant | 138.9 (Unit) | 79.1 (Unit) | 24.5 | 3 | 58 | 5 | 4 | Positive |
|  | Qual | 138.9 (Unit) | 32.2 (Unit) |  | 3 | 58 | 20 | 4 | Positive |
| Homo-L-arginine [$^{13}$C$_7$, $^{15}$N$_4$] | Quant | 200.0 (Unit) | 153.0 (Unit) | 717.1 | 3 | 88 | 5 | 2 | Positive |
|  | Qual | 200.0 (Unit) | 90.2 (Unit) |  | 3 | 88 | 20 | 2 | Positive |
| Isoleucine-[$^{13}$C$_6$] | Quant | 138.0 (Unit) | 74.2 (Unit) | 24.6 | 3 | 104 | 19 | 3 | Positive |
|  | Qual | 138.0 (Unit) | 60.2 (Unit) |  | 3 | 104 | 32 | 3 | Positive |
| L-Methionine-[$^{13}$C$_5$] | Quant | 155.0 (Unit) | 59.2 (Unit) | 40.0 | 3 | 104 | 16 | 2 | Positive |
|  | Qual | 155.0 (Unit) | 108.2 (Unit) |  | 3 | 104 | 14 | 2 | Positive |
| Asymmetric dimethylarginine [$^2$H$_6$] | Quant | 209.2 (Unit) | 52.3 (Unit) | 175.0 | 3 | 100 | 15 | 4 | Positive |
|  | Qual | 209.2 (Unit) | 70.2 (Unit) |  | 3 | 100 | 20 | 4 | Positive |
| Symmetric Dimethylarginine-[$^2$H$_6$] | Quant | 209.1 (Unit) | 175.1 (Unit) | 41.9 | 3 | 90 | 10 | 4 | Positive |
|  | Qual | 209.1 (Unit) | 164.0 (Unit) |  | 3 | 90 | 15 | 4 | Positive |
| Taurine [$^{13}$C$_2$] | Quant | 128.1 (Unit) | 46.2 (Unit) | 74.2 | 3 | 102 | 16 | 3 | Positive |
|  | Qual | 128.1 (Unit) | 110.2 (Unit) |  | 3 | 102 | 8 | 3 | Positive |
| N-Isobutyrylglycine [$^{13}$C$_2$, $^{15}$N] | Quant | 149.0 (Unit) | 43.2 (Unit) | 82.9 | 3 | 60 | 15 | 7 | Positive |
|  | Qual | 149.0 (Unit) | 79.1 (Unit) |  | 3 | 60 | 5 | 7 | Positive |
| Urea [$^{13}$C, $^{18}$O] | Quant | 64.2 (Unit) | 47.2 (Unit) | 469.3 | 3 | 100 | 25 | 2 | Positive |
|  | Qual | 64.2 (Unit) | 64.1 (Unit) |  | 3 | 100 | 0 | 2 | Positive |
| (±)-Cotinine [$^2$H$_3$] | Quant | 180.0 (Unit) | 80.0 (Unit) | 21.7 | 3 | 100 | 25 | 5 | Positive |
|  | Qual | 180.0 (Unit) | 101.0 (Unit) |  | 3 | 100 | 20 | 5 | Positive |
| L-(+)-Ergothioneine [$^2$H$_9$] | Quant | 239.0 (Unit) | 127.0 (Unit) | 122.3 | 3 | 100 | 25 | 4 | Positive |
|  | Qual | 239.0 (Unit) | 195.0 (Unit) |  | 3 | 100 | 10 | 2 | Positive |
| L-Acetylcarnitine [$^2$H$_3$] | Quant | 207.2 (Unit) | 60.1 (Unit) | 853.4 | 3 | 100 | 15 | 4 | Positive |
|  | Qual | 207.2 (Unit) | 85.0 (Unit) |  | 3 | 100 | 15 | 4 | Positive |
| L-Glutamine [$^{13}$C$_5$] | Quant | 149.9 (Unit) | 131.9 (Unit) | 24.8 | 3 | 100 | 10 | 2 | Negative |
|  | Qual | 149.9 (Unit) | 113.8 (Unit) |  | 3 | 100 | 15 | 2 | Negative | in source fragmentation

Example 8: Metabolites of Interest

TABLE 11 tabulates a non-limiting list of metabolites of interest which are considered in this application. These metabolites, and or metabolite classes, are deemed relevant by the inventors in view of identifying non-obvious prognostic combinations of metabolites, to predict risk of preeclampsia in a pregnant woman prior to appearance of clinical symptoms of preeclampsia in the woman. Where possible the metabolites of interest are identified by their CAS number, or/and their HMDB identifier; the molecular weights are also given (na: not available).

| Metabolite | Metabolite Class | HMDB | CAS | MW |
|---|---|---|---|---|
| 25-Hydroxy vitamin D$_3$ | Vitamin D and derivatives | 0003550 | CAS 63283-36-3 | 400.6371 |

TABLE 11-continued tabulates a non-limiting list of metabolites of interest which are considered in this application. These metabolites, and or metabolite classes, are deemed relevant by the inventors in view of identifying non-obvious prognostic combinations of metabolites, to predict risk of preeclampsia in a pregnant woman prior to appearance of clinical symptoms of preeclampsia in the woman. Where possible the metabolites of interest are identified by their CAS number, or/and their HMDB identifier; the molecular weights are also given (na: not available).

| Metabolite | Metabolite Class | HMDB | CAS | MW |
|---|---|---|---|---|
| 2-Hydroxybutanoic acid | (Keto- or Hydroxy) Fatty acids | 0000008 | CAS 5094-24-6 | 104.1045 |
| 2-methylglutaric acid | Dicarboxylic acids, | 0000422 | CAS 617-62-9 | 146.1412 |
| 3-Hydroxybutanoic acid | (Keto- or Hydroxy) Fatty acids | 0000357 | CAS 300-85-6 | 104.1045 |
| Adipic acid | Dicarboxylic acids | 0000448 | CAS 124-04-9 | 146.1412 |
| L-Alanine | Amino acids | 0000161 | CAS 56-41-7 | 89.0932 |
| Arachidonic acid | (Unsaturated) Fatty acids | 0001043 | CAS 506-32-1 | 304.4669 |
| L-Arginine | Amino acids | 0000517 | CAS 74-79-3 | 174.201 |
| L-Leucine | Amino acids | 0000687 | CAS 61-90-5 | 131.1729 |
| 8,11,14 Eicosatrienoic acid | (Unsaturated) Fatty acids | 0002925 | CAS 1783-84-2 | 306.4828 |
| Citrulline | Amino acids | 0000904 | CAS 372-75-8 | 175.1857 |
| Decanoylcarnitine | Carnitines | 0000651 | CAS 1492-27-9 | 315.4482 |
| Dodecanoyl-L-carnitine (C12) | Carnitines | 0002250 | CAS 25518-54-1 | 343.5014 |
| Docosahexaenoic acid | (Unsaturated) Fatty acids | 0002183 | CAS 6217-54-5 | 328.4883 |
| Dilinoleoyl-glycerol [isomer mixture of 1,3-Dilinoleoyl-glycerol and 1,2-rac-Dilinoleoyl-glycerol] | Diacylglycerols | 0007248 | CAS 15818-46-9 CAS 30606-27-0 | 616.9542 |
| Choline | Cholines | 0000097 | CAS 62-49-7 | 104.1708 |
| Glycyl-glycine | Dipeptides | 0011733 | CAS 556-50-3 | 132.1179 |
| Homo-L-arginine | Amino acids | 0000670 | CAS 156-86-5 | 188.2275 |
| Hexadecanoic acid (palmitic acid) | (Saturated) Fatty acids | 0000220 | CAS 57-10-3 | 256.4241 |
| L-Isoleucine | Amino acids | 0000172 | CAS 73-32-5 | 131.1729 |
| Linoleic acid | (Unsaturated) Fatty acids | 0000673 | CAS 60-33-3 | 280.4455 |
| L-methionine | Amino acids | 0000696 | CAS 63-68-3 | 149.211 |
| NG-Monomethyl-L-arginine | Amino acids | 0029416 | CAS 17035-90-4 | 188.2275 |
| Oleic acid | (Unsaturated) Fatty acids | 0000207 | CAS 112-80-1 | 282.4614 |
| L-Palmitoylcarnitine | Acyl carnitines | 0000222 | CAS 6865-14-1 | 399.6077 |
| Asymmetric dimethylarginine | Amino acids | 0001539 | CAS 30315-93-6 | 202.2541 |
| Sphingosine-1-phosphate | Phosphosphingolipids | 0000277 | CAS 26993-30-6 | 379.4718 |
| Sphinganine-1-phosphate (C18 base) | Phosphosphingolipids | 0001383 | CAS 19794-97-9 | 381.4877 |
| Symmetric dimethylarginine | Amino acids | 0003334 | CAS 30344-00-4 | 202.2541 |
| Taurine | Amino acids | 0000251 | CAS 107-35-7 | 125.147 |
| Isobutyrylglycine | N-acyl-alpha amino acids | 0000730 | CAS 15926-18-8 | 145.1564 |
| Urea | Amino ketones | 0000294 | CAS 57-13-6 | 60.0553 |
| Stearoylcarnitine | Acyl carnitines | 0000848 | CAS 1976-27-8 | 427.6609 |
| Eicosapentaenoic acid | (Unsaturated) Fatty acids | 0001999 | CAS 10417-94-4 | 302.451 |
| Ricinoleic acid | (Unsaturated) Fatty acids; (Keto- or Hydroxy) Fatty acids | 0034297 | CAS 141-22-0 | 298.4608 |
| 13-Oxooctadecanoic acid | (Keto- or Hydroxy) Fatty acids | na | Not available | 298.4608 |
| 3-Hydroxytetradecanoic acid | (Keto- or Hydroxy) Fatty acids | 0061656 | CAS 3422-31-9 | 244.3703 |
| 1-heptadecanoyl-2-hydroxy-sn-glycero-3-phosphocholine | Glycerophospholipids | | CAS 50930-23-9 | 509.6566 |
| Bilirubin | (Tetrapyrroles and derivatives) Bilirubins | 0000054 | CAS 635-65-4 | 584.6621 |
| Biliverdin | (Tetrapyrroles and derivatives) Bilirubins | 0001008 | CAS 114-25-0 | 582.6463 |
| Etiocholanolone glucuronide | Testosterones (androgens/steroids) | 0004484 | CAS 3602-09-3 | 466.5644 |
| Cotinine | Pyridines | 0001046 | CAS 486-56-6 | |
| Myristic acid | (Saturated) Fatty acids | 0000806 | CAS 544-63-8 | 228.3709 |
| Stearic acid | (Saturated) Fatty acids | 0000827 | CAS 57-11-4 | 284.4772 |
| 1-oleoyl-2-hydroxy-sn-glycero-3-phospho-L-serine | Glycerophospholipids | Na | CAS 326589-90-6 | 522.596 |

TABLE 11-continued tabulates a non-limiting list of metabolites of interest which are considered in this application. These metabolites, and or metabolite classes, are deemed relevant by the inventors in view of identifying non-obvious prognostic combinations of metabolites, to predict risk of preeclampsia in a pregnant woman prior to appearance of clinical symptoms of preeclampsia in the woman. Where possible the metabolites of interest are identified by their CAS number, or/and their HMDB identifier; the molecular weights are also given (na: not available).

| Metabolite | Metabolite Class | HMDB | CAS | MW |
| --- | --- | --- | --- | --- |
| L-(+)-Ergothioneine | Amino acids | 0003045 | CAS 497-30-3 | 229.299 |
| 20-Carboxy-leukotriene B4 | Eicosanoids | 0006059 | CAS 80434-82-8 | 366.4486 |
| 2-Hydroxytetradecanoic acid | (Keto- or Hydroxy) fatty acids | 0002261 | CAS 2507-55-3 | 244.3703 |
| 1-Palmitoyl-2-hydroxy-sn-glycero-3-phosphocholine (LysoPC(16:0)) | Glycerophospholipids | 0010382 | CAS 17364-16-8 | 495.6301 |
| L-Acetylcarnitine | Carnitines | 0000201 | CAS 3040-38-8 | 203.2356 |
| 6-Hydroxysphingosine | Sphingolipids | Na | Not available | 315.498 |
| L-Lysine | Amino acids | 0000182 | CAS 56-87-1 | 146.1876 |
| L-Glutamine | Amino acids | 0000641 | CAS 56-85-9 | 146.1445 |
| Sphinganine-1-phosphate (C17 base) | Phosphosphingolipids | Na | CAS 474923-29-0 | |

In order to develop the collection of analytical methods as disclosed herein, reference materials for the above metabolites were purchased from: Fluka (Arklow, Ireland), Fischer scientific (Blanchardstown, Ireland), IsoSciences (King of Prussia, PA, USA), Sigma-Aldrich (Wicklow, Ireland), Avanti Lipids (Alabaster, Alabama, USA), QMX Laboratories (Thaxted, UK), LGC (Teddington, U.K), Alfa Chemistry (Holtsville, NY, USA), Generon (Maidenhead, UK), Larodan (Solna, Sweden) and R&D Systems (Abingdon, UK). Depending on physicochemical characteristics of the metabolite of interest, sometimes a salt form of the metabolite of interest was procured.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

What is claimed herein is:

1. A method of quantitative metabolic profiling of a biological sample containing multiple metabolites representing a plurality of different metabolite classes, comprising the steps of:
pre-treating the biological sample comprising mixing the biological sample with a metabolite extraction solvent to provide a mixture, incubating the mixture to precipitate protein in the mixture, and separating the precipitated protein to provide a pre-treated sample;
providing a first aliquot and a second aliquot of the pre-treated biological sample;
separating the first aliquot of the pre-treated biological sample by reverse phase liquid chromatography (RPLC) to provide a first eluent containing resolved hydrophobic metabolites;
separating the second aliquot of the pre-treated biological sample by hydrophilic interaction liquid interaction chromatography (HILIC) to provide a second eluent containing resolved hydrophilic metabolites; and
assaying the first eluent and second eluent using targeted tandem mass spectrometry operated in multiple reaction monitoring mode to quantitatively profile the metabolites representing the plurality of different metabolite classes;
in which the metabolite extraction solvent comprises methanol, isopropanol, and an acetate buffer and in which the mixture of biological sample and metabolite extraction solvent is incubated at a temperature of less than 10° C. for a period of time to assist protein precipitation, prior to separation of the precipitated protein.

2. The method according to claim 1, in which each chromatography (LC) is directly hyphenated with the tandem mass spectrometry (MS/MS) into a single LC-MS/MS analysis.

3. The method according to claim 1, in which the extraction solvent comprising methanol, isopropanol, and an acetate buffer in a ratio of about 10:9:1 (v/v/v).

4. The method according to claim 1, in which the extraction solvent comprises 0.01 to 0.1% butylated hydroxytoluene (BHT) (m/v).

5. The method according to claim 1, in which the mixture of biological sample and extraction solvent is incubated at a temperature of less than 5° C. for a period of time to assist protein precipitation, prior to separation of the precipitated protein.

6. The method according to claim 1, in which the biological sample is a liquid sample and is collected and stored on a volume controlling sampling device.

7. The method according to claim 1, in which the tandem mass spectrometry comprises electrospray ionization.

8. The method according to claim 1, in which the tandem mass spectrometry comprises electrospray ionization carried out under both positive and negative electrospray ionization.

9. The method according to claim 1, in which the RPLC employs a varying mixture of a first mobile phase comprising water, methanol, and an acetate buffer and a second mobile phase comprising methanol, acetonitrile, isopropanol, and an ammonium acetate buffer.

10. The method according to claim 9, in which the first mobile phase and second mobile phase are mixed according to a linear gradient of about 0% to 100% of the second mobile phase over a period of about 8-12 minutes.

11. The method according to claim 1, in which the HILIC employs a varying mixture of a first mobile phase comprising ammonium formate and a second mobile phase comprising acetonitrile.

12. The method according to claim 11, in which the mobile phases are mixed according to a linear gradient of about 88% to 50% the second mobile phase over a period of 8-12 minutes.

13. The method according to claim 1, in which the biological sample comprises one or more stable isotope-labelled internal standards (SIL-IS) corresponding to one or more metabolites.

14. The method according to claim 13, in which the plurality of metabolites represent a plurality of metabolite classes selected from acetyls, acyclic alkanes, acyl carnitines, aldehydes, amino acids, amino ketones, aralkylamines, benzene and substituted derivatives, tetrapyrols and derivatives, biphenyls and derivatives, carnitines, cholines, corticosteroids and derivatives, coumarins and derivatives, diacylglycerols, dicarboxylic acids, dipeptides, eicosanoids, fatty acids, glycerophospholipids, hydroxy acids and derivatives, monosaccharide phosphates, N-acyl-alpha amino acids, phenylpropanoic acids, phosphosphingolipids, azacyclic compounds, sphingolipids, sugar alcohols, androgens and steroids, Vitamin D, and derivatives of any of the foregoing.

15. The method according to claim 14, wherein the plurality of metabolites comprises a fatty acid and in which the fatty acid is selected from hydroperoxyl fatty acids, keto- or hydroxy-fatty acids, saturated fatty acids, unsaturated fatty acids, or epoxy fatty acids.

16. The method according to claim 14, wherein the plurality of metabolites comprises an azacylic compound and in which the azacyclic compound is a pyridine.

17. The method according to claim 14, wherein the plurality of metabolites comprises a steroid and in which the steroid is a testosterone.

* * * * *